(12) United States Patent
Compel et al.

(10) Patent No.: US 9,683,992 B2
(45) Date of Patent: Jun. 20, 2017

(54) LIGAND PASSIVATED GOLD NANOPARTICLES

(71) Applicants: William S. Compel, Fort Collins, CO (US); Christopher J. Ackerson, Fort Collins, CO (US); On Lo A. Wong, Fort Collins, CO (US)

(72) Inventors: William S. Compel, Fort Collins, CO (US); Christopher J. Ackerson, Fort Collins, CO (US); On Lo A. Wong, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 14/448,789

(22) Filed: Jul. 31, 2014

(65) Prior Publication Data

US 2015/0037585 A1   Feb. 5, 2015

Related U.S. Application Data

(60) Provisional application No. 61/860,566, filed on Jul. 31, 2013, provisional application No. 62/012,496, filed on Jun. 16, 2014.

(51) Int. Cl.
| | |
|---|---|
| *C22F 1/14* | (2006.01) |
| *B32B 5/16* | (2006.01) |
| *G01N 33/543* | (2006.01) |
| *B82B 3/00* | (2006.01) |

(52) U.S. Cl.
CPC ....... *G01N 33/54346* (2013.01); *B82B 3/009* (2013.01); *C22F 1/14* (2013.01); *Y10T 428/2982* (2015.01)

(58) Field of Classification Search
CPC .................................. B82B 3/009; C22F 1/14
USPC .................................. 428/403; 977/810, 834
See application file for complete search history.

(56) References Cited

U.S. PATENT DOCUMENTS

| | | | |
|---|---|---|---|
| 8,304,257 B2 * | 11/2012 | Ackerson ............. | B22F 1/0018 436/525 |
| 2003/0118729 A1 * | 6/2003 | Bishop et al. ................ | 427/256 |
| 2007/0269594 A1 * | 11/2007 | Ackerson et al. ............ | 427/216 |
| 2009/0258202 A1 * | 10/2009 | Sakaguchi et al. ........... | 428/206 |
| 2011/0175040 A1 * | 7/2011 | Sakaguchi et al. ........... | 252/514 |
| 2013/0095320 A1 * | 4/2013 | Sano et al. .................... | 428/402 |

OTHER PUBLICATIONS

Walter et al, A unified view of ligand-protected gold clusters as superatom complexes, PNAS, Jul. 2008, vol. 105, No. 27, 9157-9162.*

(Continued)

*Primary Examiner* — Holly Le
(74) *Attorney, Agent, or Firm* — Haukaas Fortius PLLC; Michael H. Haukaas

(57) ABSTRACT

The invention provides novel gold nanoclusters of the formula $Au_{20}(SR)_{15}$(weak ligand), wherein each R is independently an organic group, and the weak ligand is a weakly associating gold ligand of Formula I as described herein. The nanocluster can have an approximate molecular weight of 6 kDa. Corresponding dimers of the nanocluster can have an approximate molecular weight of 10 kDa (by SEC). The invention also provides methods of making and using the gold nanoclusters.

21 Claims, 11 Drawing Sheets

(56) References Cited

OTHER PUBLICATIONS

Zhu et al., Thiolate-Protected Au20 Clusters with a Large Engergy Gap of 2.1 eV, J.A.C.S. 2009, 131, 7220-7221.*
Schulz-Dobrick et al., Surfactant-Free Synthesis and Functionalization of Gold Nanoparticles, J.A.C.S. 2005, 127, 12816-12817.*
Dharmaratne et al., J.A.C.S. 2009, 131, 13604-13605.*
Ackerson, Christopher et al., "Thiolate Ligands for Synthesis of Water-Soluble Gold Clusters," Journal of the American Chemical Society, 127, Apr. 16, 2005, pp. 6550-6551.
Ackerson, Christopher J. et al.,"Rigid, Specific, and Discrete Gold Nanoparticle/Antibody Conjugates," Journal of the American Chemical Society, 128, Feb. 2, 2006, pp. 2635-2640.
Ackerson, Christopher J. et al., "Site-Specific Biomolecule Labeling with Gold Clusters," Methods in Enzymology, vol. 241, Chap. 9, 2010, pp. 195-230.
Koivisto, Jaakko et al., "Vibrational Perturbations and Ligand-Layer Coupling in a Single Crystal of Au144 (SC2H4Ph)60 Nanocluster," Journal of Physical Chemistry Letters, 5, Jan. 3, 2014, pp. 387-392.
Meng, Xianming et al., "Controlled reduction for size selective synthesis of thiolate-protected gold nanoclusters Aun(n=20, 24, 39, 40)," Nanoscale Research Letters, 7:277, 2012, 7 pp.
Negishi, Yuichi et al., "Glutathione-Protected Gold Clusters Revisited: Bridging the Gap between Gold(I)-Thiolate Complexes and Thiolate-Protected Gold Nanocrystals," Journal of the American Chemical Society, 127, Mar. 18, 2005, pp. 5261-5270.
Pei, Yong et al., "Interlocked Catenane-Like Structure Predicted in Au24(SR)20: Implication to Structural Evolution of Thiolated Gold Clusters from Homoleptic Gold(I) Thiolates to Core-Stacked Nanoparticles," Journal of the American Chemical Society, 134, Jan. 15, 2012, pp. 3015-3024.
Pei, Yong et al., "Thiolate-Protected Au20(SR)16 Cluster: Prolate Au8 Core with New [Au3(SR)4] Staple Motif," Journal of the American Chemical Society, 131, Sep. 2, 2009, pp. 13619-13621.
Tofanelli, Marcus A. et al., "Superatom Electron Configuration Predicts Thermal Stability of Au25(SR)18 Nanoclusters," Journal of the American Chemical Society, 134, Sep. 26, 2012, pp. 16937-16940.
Tsukuda, Tatsuya, "Toward an Atomic-Level Understanding of Size-Specific Properties of Protected and Stabilized Gold Clusters," Bull. Chem. Soc. Jpn., vol. 85, No. 2, Feb. 10, 2012, pp. 151-168.
Wang, L. et al., "Dynamic Nanoparticle Assemblies", Accounts of Chemical Research, vol. 45, No. 11, Mar. 26, 2012, pp. 1916-1926.
Wong, O. Andrea et al., "Structure-activity relationships for biodistribution, pharmacokinetics, and excretion of atomically precise nanoclusters in a murine mode," Nanoscale, 5, Jun. 17, 2013, pp. 10525-10533.
Zeng, Chenjie et al., "Chiral Structure of Thiolate-Protected 28-Gold-Atom Nanocluster Determined by X●ray Crystallography," Journal of the American Chemical Society, 135, Jul. 1, 2013, pp. 10011-10013.

* cited by examiner

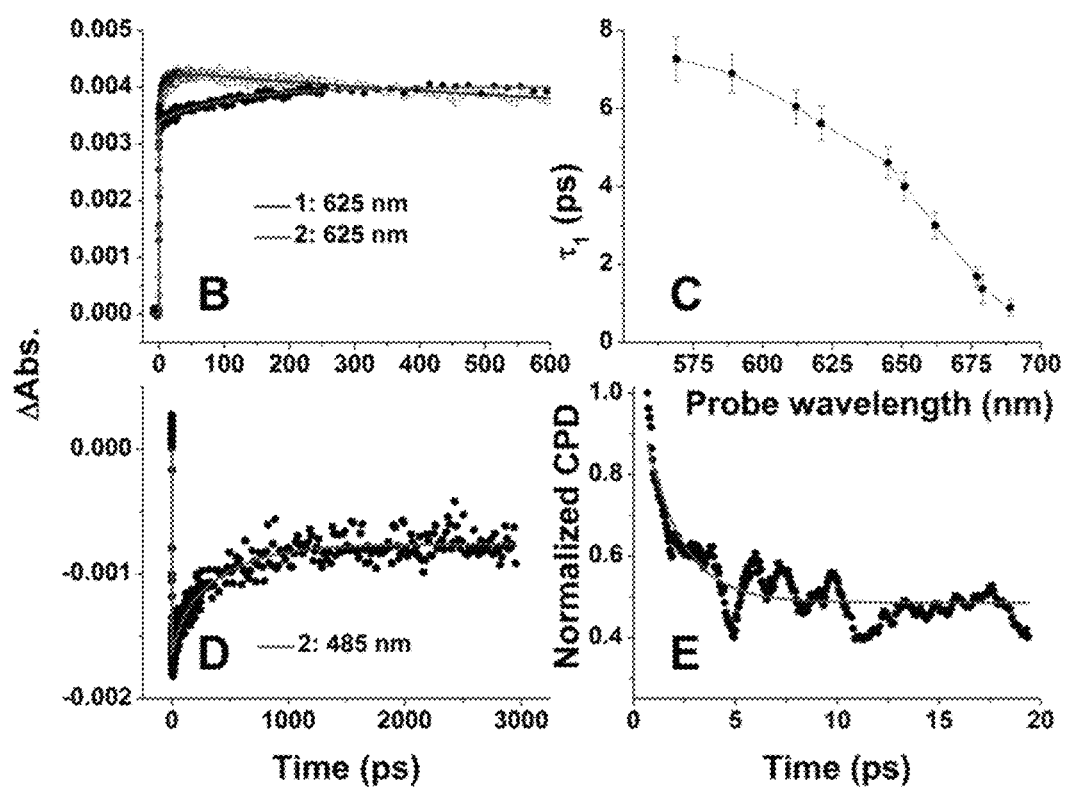
Figure 12B-E

LIGAND PASSIVATED GOLD NANOPARTICLES

RELATED APPLICATIONS

This application claims priority under 35 U.S.C. §119(e) to U.S. Provisional Patent Application Nos. 61/860,566 filed Jul. 31, 2013 and Ser. No. 62/012,496 filed Jun. 16, 2014, which applications are incorporated herein by reference.

BACKGROUND OF THE INVENTION

The self-assembly of metal nanoparticles driven by interactions of surface-anchored ligands such as DNA, multivalent thiolates, and proteins results in 1-, 2- and 3-dimensional nanoparticle superstructures. Such superstructures display emergent fundamental optical properties. Applications in sensing, plasmonics and biology arise from ensemble properties absent in discrete metal nanoparticles.

In the case of the widely studied gold nanoparticle assembly, the assembly is almost always mediated by thiol-anchored ligands. This results in largely static and stable assemblies, due to the comparatively strong Au—S bond precluding dynamic events. Any dynamic aspects of the assembly arise from plasticity within the ligand. However, new gold nanoparticle assemblies that have intense fluorescent properties and increased intensity of paramagnetic behavior are needed for practical applications.

Monolayer-protected thiolated gold nanoclusters are stable metal nanoparticles that are passivated by a layer of organic material. They have attracted much attention since their first description about 15 years ago due to their interesting physiochemical properties and their potential applications in bioimaging and theranostics. Most known syntheses of these gold nanoclusters result in products that have noble-gas-like superatomic electron configuration, such as $Au_{25}(SR)_{18}^-$ and $Au_{102}(SR)_{44}$. The gold nanoclusters that correspond to the closed-shell configuration are the results of thermodynamic stabilization. The synthesis of new gold nanoclusters with different molecular compositions should provide new and enhanced properties that could provide additional applications such as bioimaging and theranostics. Thus, there is a need for novel nanoclusters that display enhanced properties such as increased quantum yield of fluorescence and extended lifetime so that the nanoclusters offer better performance in these applications.

SUMMARY

The invention provides gold nanoclusters and the dynamic ligand-mediated self-assembly of dimers thereof. The gold nanocluster dimers can self-assemble in the presence of a non-thiolate weak gold ligand into discrete and dynamic structures. Various $Au_{20-28}(SR)_{15-19}$-(weak ligand) nanoclusters can be formed into $Au_{20-28}(SR)_{15-19}$-(weak ligand)-$Au_{20-28}(SR)_{15-19}$ nanoclusters, where SR is the thiolate of a thiol. Models validated by transient absorption spectroscopy indicate a low-spin monomer and a high-spin dimer, with assembly enabled through weak ligand oxygen-gold interactions. Close spatial coupling allows electron delocalization between the nanoparticle cores. The resulting assemblies possess important optical, electronic, and structural properties.

Accordingly, the invention provides a gold nanocluster of the formula $Au_x(SR)_y$(weak ligand), wherein x is 20-28, y is 15-19, each R is independently an organic group comprising 1-30 carbon atoms covalently bound to the sulfur atom of the group SR, and the weak ligand is a weakly associating gold ligand of Formula I:

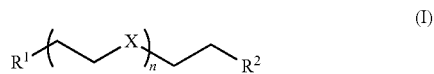

wherein
X is O, S, $CH_2$, NH, or PH;
$R^1$ and $R^2$ are each independently OH, OMe, OEt, SH, SMe, SEt, $NH_2$, NHMe, $NMe_2$, NHEt, $NEt_2$, $PH_2$, PHMe, $PMe_2$, PHEt, or $PEt_2$; and
n is 1, 2, 3, 4, or about 5 to about 50. The nanocluster can have an approximate molecular weight of 6 kDa and can be yellow in color upon isolation. Dimers of these gold nanoclusters can also be prepared. Thus, the gold nanoparticle having one weak ligand can further comprise a second gold nanocluster, thereby forming a discrete gold nanocluster of the formula $(Au_{20}(SR)_{15})_2$(weak ligand). The 'dimer' nanocluster can have an approximate molecular weight of 10 kDa (as determined by size exclusion chromatography) and can be orange in color upon isolation.

In some embodiments, the monomer gold nanocluster is water-soluble. In further embodiments, the dimer gold nanocluster is water-soluble. In some embodiments, the monomer gold nanocluster is organo-soluble. In further embodiments, the dimer gold nanocluster is organo-soluble.

In some embodiments, x can be 20, 21, 22, 23, 24, 25, 26, 27, or 28. In various embodiments, y can be 15, 16, 17, 18, or 19. In certain specific embodiments, x is 20 and y is 15. In another specific embodiment, x is 24 and y is 17, or x is 25 and y is 17. In yet other specific embodiments, x is 28 and y is 19. Gold nanoclusters that include organo-soluble thiolate ligands (SR) are often nanoclusters where x is 20 and y is 15. In other embodiments, the gold nanoclusters that include organo-soluble thiolate ligands (SR) such as PET are often nanoclusters where x is x is 24 and y is 17, or where x is 28 and y is 19. Gold nanoclusters that include water-soluble thiolate ligands (SR) such as glutathione, thiomalic acid, and p-mercaptobenzoic acid, are often nanoclusters where x is 25 and y is 17. Such compounds can be identified and characterized by, for example, MALDI-MS, optical spectroscopy, and PAGE.

In some embodiments, each $R^1$ and $R^2$ is OMe. In various embodiments, n can be 1, 2, or 3. In certain specific embodiments, the weak ligand of Formula I is diethylene glycol dimethyl ether, triethylene glycol dimethyl ether, or tetraethylene glycol dimethyl ether.

In some embodiments, —SR is the thiolate of glutathione, cysteine, captopril, thiomalic acid, N-(2-mercaptopropionyl) glycine, p-mercaptobenzoic acid, m-mercaptobenzoic acid, furan-2-ylmethanethiol, penicillamine, a $(C_2-C_7)$mercaptoalkanoic acid, 2-phenylethanethiol (PET), 1-phenylethanethiol, benzyl mercaptan, thiophenol, a $(C_1-C_{18})$alkylthiol, a $(C_3-C_8)$ mercaptocycloalkane, a $(C_8-C_{18})$ mercaptoalkanoic acid, dimercaptosuccinic acid, 2-mercaptoethanol, 3-mercaptopropanol, 3-mercaptopropane-1,2-diol, 1-adamantanethiol, 1-naphthalenethiol, 2-naphthalenethiol, or camphorthiol. In certain, specific embodiments, —SR is the thiolate of glutathione or phenylethanethiol (PET).

The quantum yield of a plurality of nanoclusters can be at least about $2 \times 10^{-3}$ or at least about $2.5 \times 10^{-3}$. In other embodiments, the quantum yield of a plurality of the nanoclusters is about $2\times10^{-3}$ to about $4\times10^{-3}$, about $2.5\times10^{-3}$ to about $3.5\times10^{-3}$, or about $3\times10^{-3}$.

The diameter of the nanoclusters can be about 0.5 nm to about 1.5 nm as monomers, or about 0.9 nm to about 2.5 nm as dimers.

In one specific embodiment, the invention provides a gold nanocluster of the formula $Au_{20}(SC_2H_4Ph)_{15}$(diethylene glycol dimethyl ether), wherein the nanocluster has an approximate molecular weight of 6 kDa and is yellow in color upon isolation. The gold nanocluster can further comprise a second gold nanocluster, thereby forming a discrete gold nanocluster of the formula $(Au_{20}(SC_2H_4Ph)_{15})_2$(diethylene glycol dimethyl ether), wherein the nanocluster has an approximate molecular weight of 10-12 kDa (as determined by size exclusion chromatography) and is orange in color upon isolation.

In another specific embodiment, the invention provides a gold nanocluster of the formula $Au_{25}(SG)_{17}$(diethylene glycol dimethyl ether), wherein SG is the thiolate of glutathione, and the nanocluster has an approximate molecular weight of 6 kDa and is yellow in color upon isolation. The gold nanocluster can further comprise a second gold nanocluster, thereby forming a discrete gold nanocluster of the formula $(Au_{25}(SG)_{17})_2$(diethylene glycol dimethyl ether), wherein the nanocluster has an approximate molecular weight of 10-12 kDa (as determined by size exclusion chromatography) and is orange in color upon isolation.

The invention also provides methods of preparing the gold nanoclusters described above and herein. The methods can include combining a gold compound, a thiol, and a weak ligand to form a first mixture, and contacting the first mixture with a reducing reagent to thereby form the gold nanocluster. The methods can further include isolating the gold nanoclusters to provide a solid composition of the gold nanoclusters.

These gold nanoclusters can provide nanoparticles with intense fluorescent properties and increased intensity of paramagnetic behavior compared to other similarly sized gold clusters such as $Au_{25}(GS)_{18}$. The products can be readily soluble in water, which makes them valuable candidates for biological studies.

The invention thus provides novel gold nanoclusters as described herein, intermediates for the synthesis of gold nanoclusters, as well as methods of preparing gold nanoclusters. The invention also provides gold nanoclusters that are useful as intermediates for the synthesis of other useful particles and reagents. The gold nanoclusters can be isolated and purified, and/or they can be used in a composition that includes a solvent, diluent, or a conjugate to other particles.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3A shows the size exclusion chromatography of 1 (far right peak) and 2 (second peak from left) relative to the well-known gold nanoparticles $Au_{144}(PET)_{60}$ (left peak) and $Au_{25}(PET)_{18}$ (second peak from right). FIGS. 3B and 3C show the MALDI mass spectrum of 1 and 2, respectively.

FIG. 5A shows linear absorption of 1 and 2 as both measured and calculated for a monomer-dimer model (1 experimental=lower solid line; 2 experimental=upper solid line; 1 simulation≤lower dashed line; 2 simulation=upper dashed line). Relaxed structures of 1 and 2 used to calculate theoretical spectra are shown below the legend. FIG. 5B shows first order decay of an isolated dimer into monomer, starting at different concentrations (top line to bottom line=100 μM, 80 μM, 60 μM, and 40 μM, respectively). The concentration dependence of the decay indicates an equilibrium between the reactant and product.

DETAILED DESCRIPTION

Figure 1:
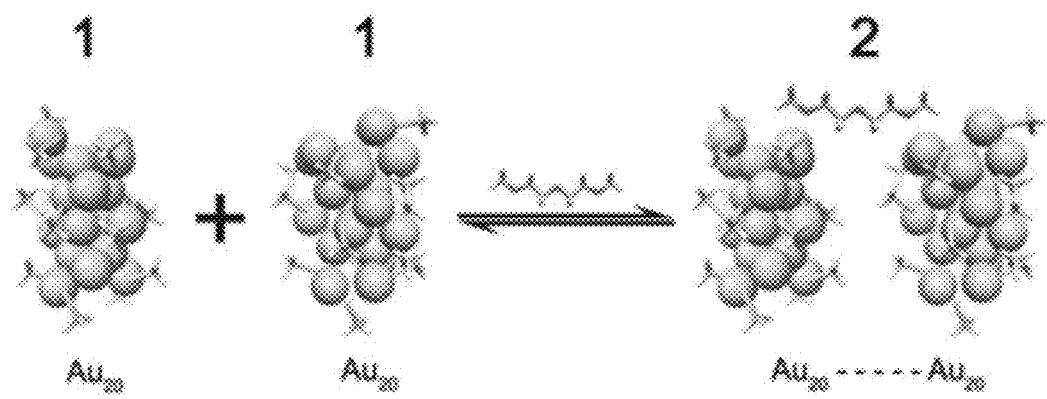
FIG. 1. Assembly of gold nanoparticles by the non-thiolate ligand diglyme into discrete and dynamic structures: $Au_{20}(SC_2H_4Ph)_{15}$-diglyme into $Au_{20}(SC_2H_4Ph)_{15}$-diglyme-$Au_{20}(SC_2H_4Ph)_{15}$.

The invention provides novel assemblies of gold nanoclusters. The gold nanoclusters can be assembled using non-thiolate weak ligands, such as diglyme, enabling the formation of the nanoclusters into discrete and dynamic structures. To understand this surprising phenomenon, the assembly of $Au_{20}(SC_2H_4Ph)_{15}$-diglyme (1) into $Au_{20}(SC_2H_4Ph)_{15}$-diglyme-$Au_{20}(SC_2H_4Ph)_{15}$ (2) was explored in detail. The assembly was validated by size exclusion chromatography, mass spectrometry, IR spectroscopy, and calorimetry. A dissociation constant of 20.4 µM was established for dimer to monomer conversion of 1 into 2 (FIG. 1). Theoretical models validated by transient absorption spectroscopy predict a low-spin monomer and a high-spin dimer, with assembly enabled through weak oxygen-gold interactions. Close spatial coupling allows electron delocalization between the nanoparticle cores. The resulting assemblies thus possess important optical, electronic, and structural properties.

Figure 2:
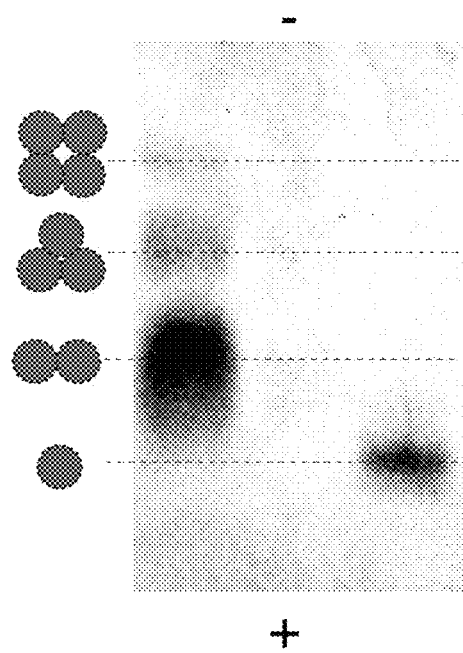
FIG. 2. PAGE image of post-synthetic self-assembly of glutathione-protected AuNCs. The purified AuNC, seen on the right of the gel, was exposed to diglyme and heat to produce the assembled structures seen on the left of the gel.

In a synthetic screen that included diethylene glycol dimethyl ether (diglyme, dg) as a co-solvent, we observed unusual post-synthetic self-assembly of products synthesized in the presence of diglyme (FIG. 2). The assembly into dynamic higher-order structures appears independent of the R-group of SR-ligands, as we observe this diglyme-correlated assembly with different sized clusters that are protected by both organic-soluble and water-soluble ligands.

The synthesis of 2-phenylethanethiol (PET)-protected Au nanoclusters (AuNC) in a diglyme/THF solvent system results in two major products. These products, which are yellow (1) and orange (2) under ambient lab lighting, are isolable from higher order assemblies and other reaction side products by silica gel chromatography. The AuNCs are stable as dry powders. The AuNC products interconvert in solution to form a mixture of 1 and 2. Size exclusion chromatography (SEC) indicates approximate molecular weights of 6.0 kDa and 10.0 kDa for 1 and 2 (FIG. 3A).

Figure 3:
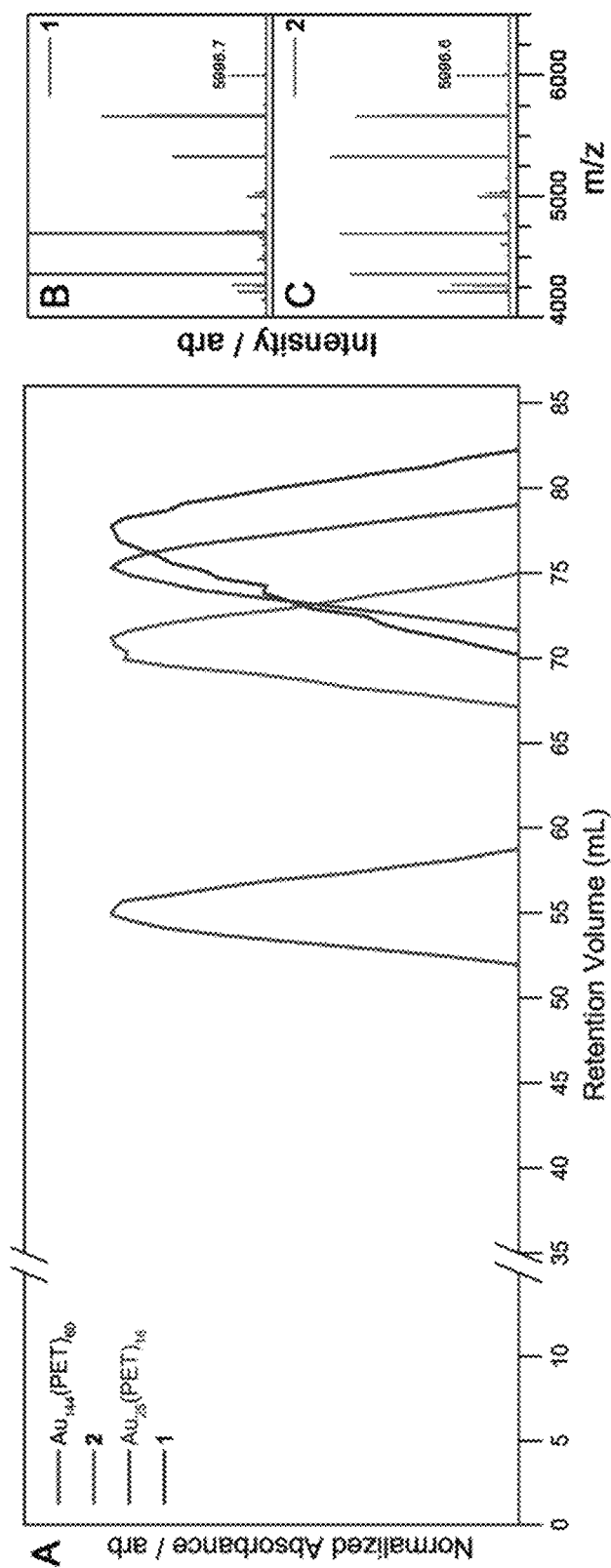
FIG. 3. The size and mass of products 1 and 2 as determined by size exclusion chromatography and mass spectrometry.
Figure 4:
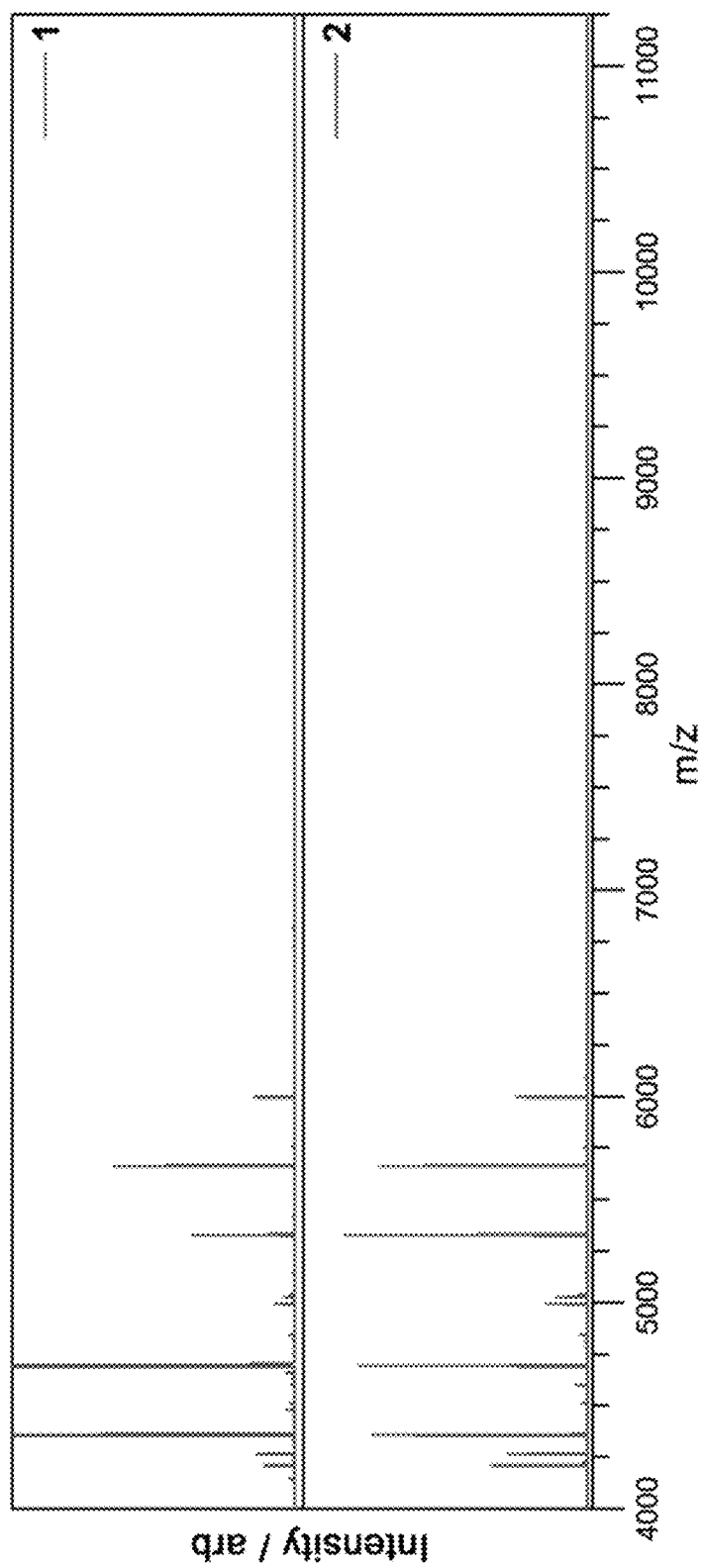
FIG. 4. Full MALDI spectra of 1 and 2. Peak masses correspond to $Au_{20}(PET)_{15}$ with lower peaks corresponding to expected —Au(SR) fragments. Lack of peaks higher than 6000 m/z indicates that the samples studied were pure.

Matrix-assisted laser desorption ionization (MALDI) mass spectrometry on each product yields identical spectra when analyzed under the same instrumental parameters (FIG. 3B, 3C). The parent peaks for 1 and 2 are at 5996.7 and 5996.6 m/z, respectively, and no other peaks are apparent at higher m/z (FIG. 4). All peaks at lower m/z are assignable as laser induced fragments of the parent. The parent peaks correspond to the formula $Au_{20}(PET)_{15}$, which has a mass of 5997.7 Da. The theoretical isotope pattern for $Au_{20}(PET)_{15}$ agrees with the experimentally obtained spectrum.

The difference between the apparent masses determined by MALDI and SEC methods and the interconversion between 1 and 2 indicates a model of dimerization of 1 into 2. This surprising model was validated by establishing the thermodynamic equilibrium constant for the interaction, by changes in the infrared spectrum consistent with the model, and by differential scanning calorimetry.

Differences in the optical spectra of 1 and 2 enable assignment of the relative fraction of each in a mixture. FIG. 5A shows the measured spectra for each product. The unique peak of 2 at 484 nm enables quantitative determination of relative concentration of 1 and 2 through Beer's law, using the empirically determined extinction coefficients of $\epsilon_{484,1}=2583$ $M^{-1}$ $cm^{-1}$ and $\epsilon_{484,2}=15347$ $M^{-1}$ $cm^{-1}$ (see Example 1 for additional details).

Solutions of isolated 2 at various concentrations were allowed to equilibrate in sealed vessels with periodic monitoring. FIG. 5B shows the decreasing concentration of 2 due to dissociation into 1 as equilibrium is approached. From this data we determined a dissociation constant ($K_d$) of 20.4±1.88 µM when starting from 2, by kinetic analysis in COPASI (see Hoops et al., *Bioinformatics* 2006, 22, 3067).

Figure 6:
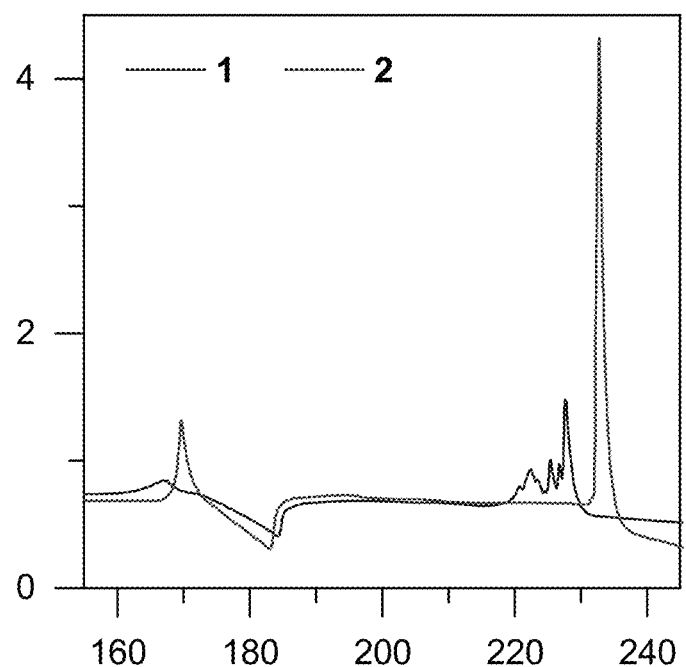
FIG. 6. DSC traces of 1 and 2 (where 2 is shown having the tallest peak). 1.5 mg of 1 and 2 were heated at a ramp of 10° C./min with $N_2$ flow rate of 90 mL/min. The exotherm evident in 2 at 170° C. corresponds to the dimer breaking. Both 1 and 2 then behave the same after the dimer is broken, exhibiting diglyme loss at 185° C. and subsequent cluster degradation ca. 220-235° C.

Analysis of both products by differential scanning calorimetry (DSC) shows an exotherm peak at 233° C., which was assigned as thermal degradation of the cluster (FIG. 6). An endotherm is observed for both samples at 180° C., which is likely the desorption of diglyme from the cluster. Product 2 shows an additional exotherm at 170° C., which exotherm is likely the breaking of the $Au_{20}$ dimer.

Figure 7:
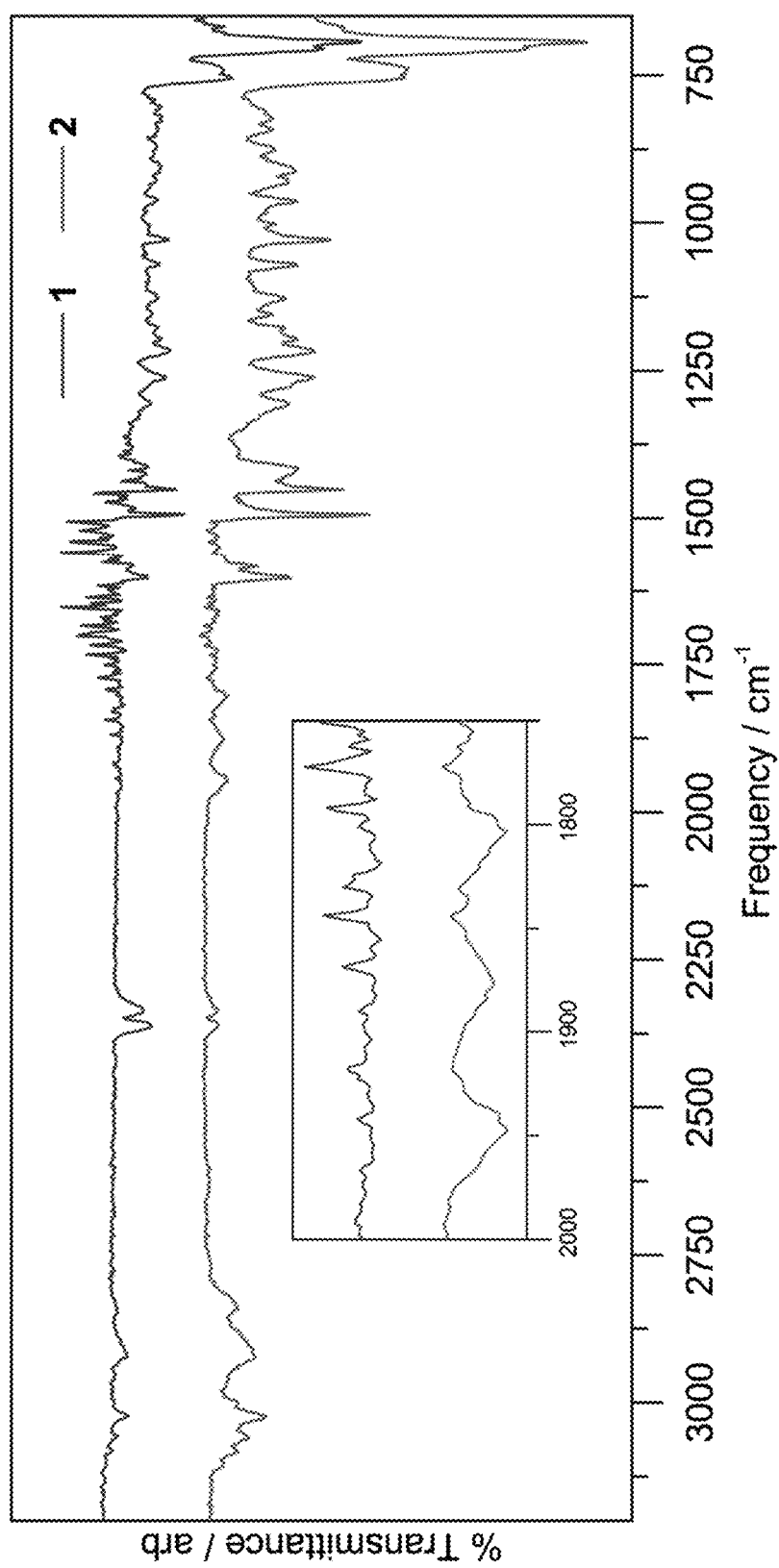
FIG. 7. Full IR spectra of 1 (top line) and 2 (bottom line), where 2 is offset for clarity. Spectra appear identical with the exception of the set of peaks at 1750-2000 $cm^{-1}$ present in 2 and absent in 1 (inset), which correspond to the forced ligand-ligand interactions caused by dimerization.

Recent work by Pettersson shows that $Au_{144}(PET)_{60}$ in a semi-crystalline state exhibits strong ligand-layer vibrational coupling that results in an increase in intensity of some vibrations as compared to the cluster in solution (Koivisto et al., *J. Phys. Chem. Lett.* 2014, 5, 387). In particular, the crystalline product exhibits three peaks in the region of 1750-2000 $cm^{-1}$ that are not apparent in solution phase. We observe similar emergent features in the same region in 2 that are lacking in 1 (FIG. 7). The increased vibrational coupling is expected, in 2 due to the forced proximity of ligands in the bridging site of the dimer.

Figure 8:
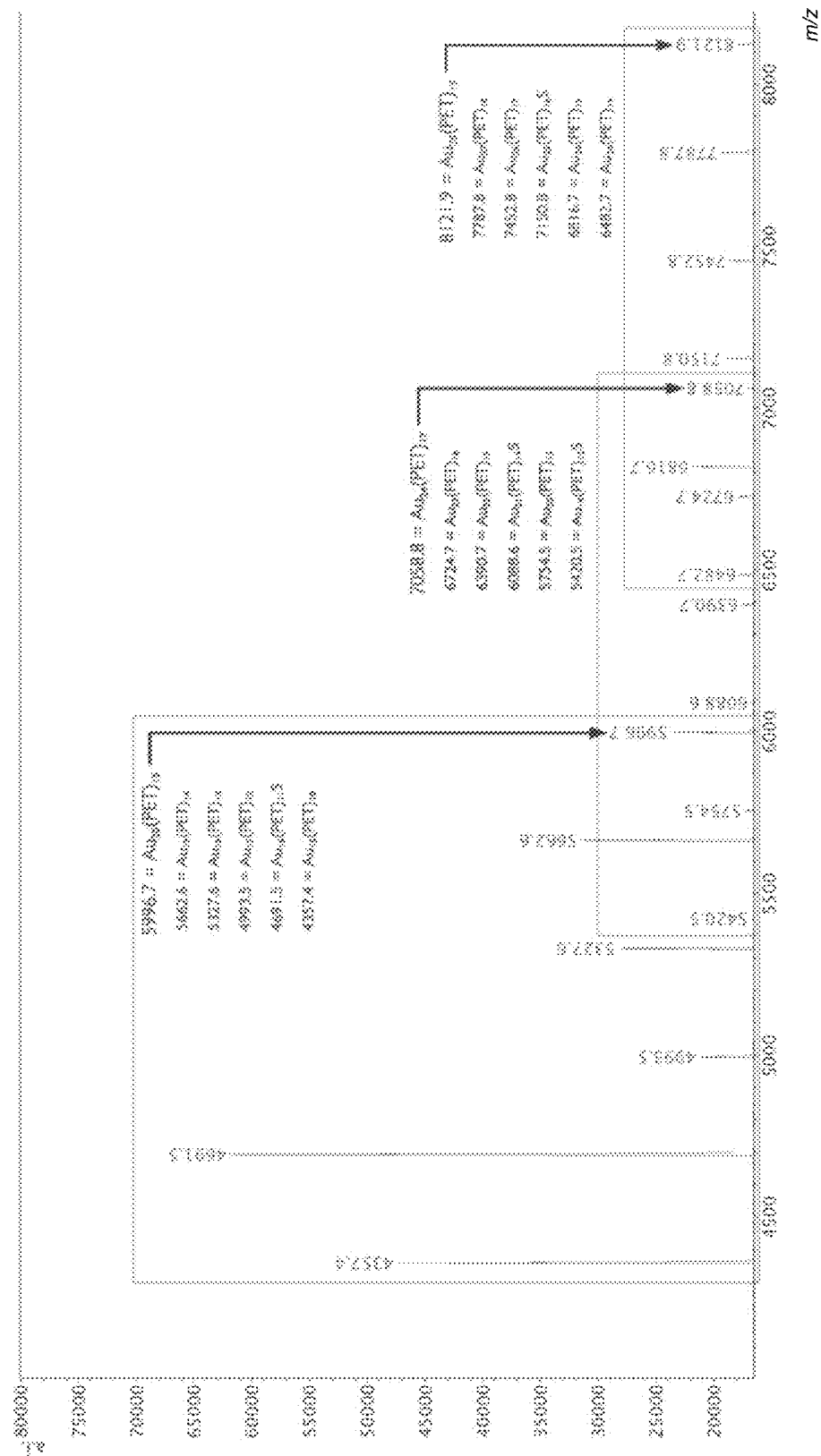
FIG. 8. Simplified MALDI spectrum of crude Au@PET synthesized in the presence of diglyme. The three parent peaks correspond to $Au_{20}(PET)_{15}$, $Au_{24}(PET)_{17}$, and $Au_{28}(PET)_{19}$. Fragmentation patterns of roughly —Au(SR) are grouped to match their parent peak ($Au_{20}(PET)_{15}$=left set; $Au_{24}(PET)_{17}$=middle set; $Au_{28}(PET)_{19}$=right set), and their corresponding $Au_x(SR)_y$ is listed with the mass of each fragment.

The most similar $Au_x(SR)_y$ cluster to the $Au_{20}(SR)_{15}$ described herein is the $Au_{20}(SR)_{16}$ reported by Jin and co-workers (Zhu et al., *J. Am. Chem. Soc.* 2009, 131, 7220) and modeled by Zeng and co-workers (Pei et al., *J. Am. Chem. Soc.* 2009, 131, 13619). $Au_{20}(PET)_{15}$ is missing a single thiolate ligand from the known $Au_{20}(SR)_{16}$. In other mass spectrometry experiments on $Au_x(SR)_y$ nanoclusters synthesized in diglyme in our modified conditions (FIG. 8), we observe x/y=24/17 and x/y=28/19, which are also one-ligand deletions of previously reported clusters x/y=24/18 and 28/20 (Pei et al., *J. Am. Chem. Soc.* 2012, 134, 3015; Zeng et al., *J. Am. Chem. Soc.* 2013, respectively). Thus the invention provides methods to prepare novel gold nanoclusters having a weak gold nanoparticle ligand, and dimers linked by the weak gold nanoparticle ligand, where in the dimers, the weak gold nanoparticle ligand takes the place of a thiolate ligand on each of the monomeric nanoparticles of the dimer. In some embodiments, the linking ligand (the weak ligand) can be a non-thiolate ligand (e.g., where sulfur is excluded from the composition of the weak ligand).

A model consistent with the mass spectroscopy, SEC, and dynamics data discussed above is one where the synthetic co-solvent diglyme, in which these AuNCs are synthesized, replaces or takes the place of a thiolate ligand in the ligand shell. In this model, the terminal methoxy group serves as a weak-ligand, whose interaction with the AuNC surface is driven by a large molar excess of diglyme as the synthetic solvent (e.g., about 100-200 equivalents of dimethoxy-containing solvent). A useful technique was to use the weak ligand in combination with an organic solvent such as THF in a ratio of about 1:1 to about 10:1 weak ligand:organic solvent. Typically the solvent system was about 75% weak ligand (e.g., diglyme) and 25% organic solvent (e.g., a cyclic ether solvent such as THF or THP; other solvents such as DMF or DMSO). Initial association among clusters may be driven in part by poor solvation of clusters by diglyme, resulting in clusters of nanoparticles, consistent with our observation that the nanoparticles are insoluble in pure diglyme. Within the cluster-of-clusters diglyme and similar weak ligands described herein can subsequently become a crosslinker. Thus, the aggregate evidence indicates 1 as $Au_{20}(PET)_{15}dg$ and 2 as $Au_{20}(PET)_{15}\text{-}dg\text{-}Au_{20}(PET)_{15}$ (a diglyme bridged cluster-of-clusters).

Figure 9:
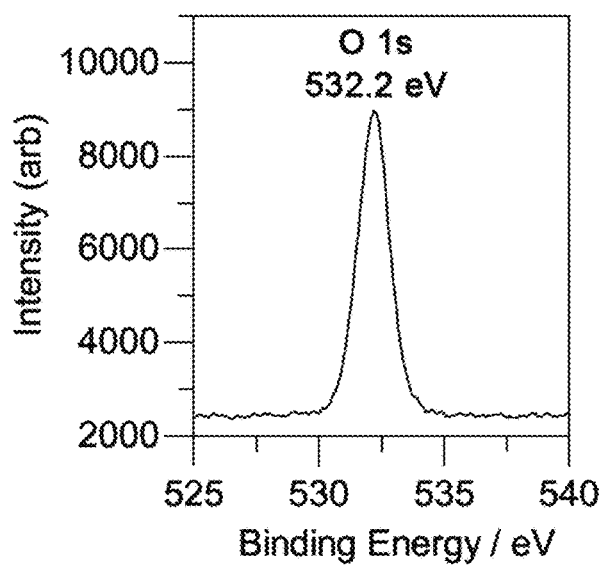
FIG. 9. X-ray photoelectron spectrum of 1 and 2 mixture on a stainless steel substrate. Existence of O 1s peak confirms presence of oxygen in Au clusters. Charge calibrated to adventitious C1s at 284.4 eV.
Figure 10:
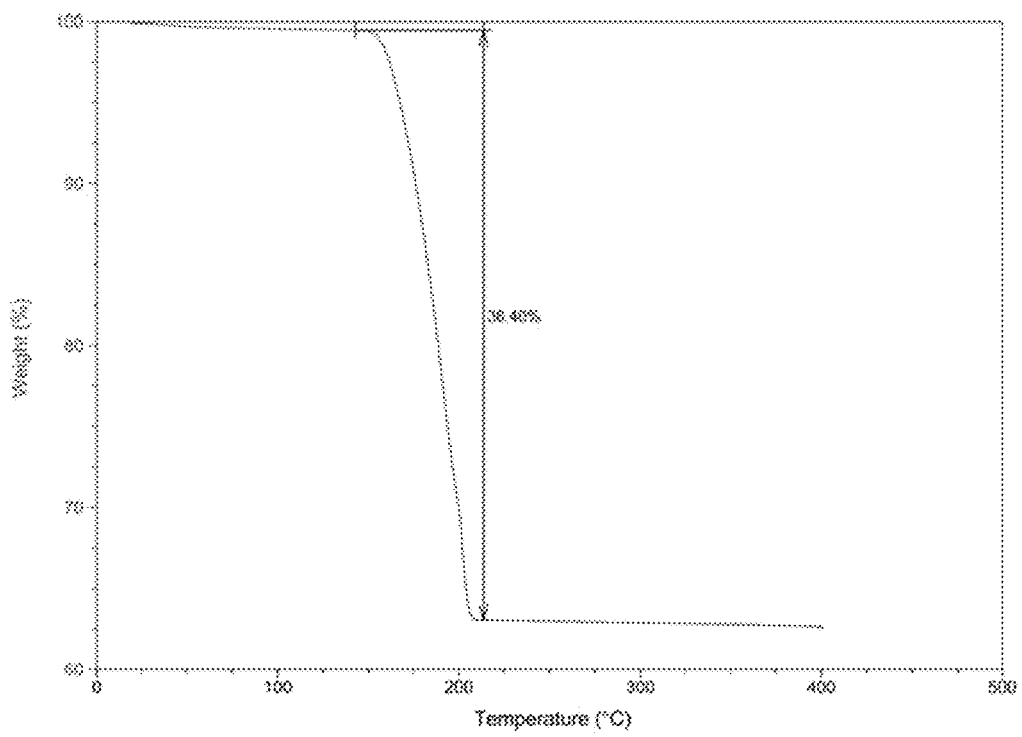
FIG. 10. Thermogravimetric analysis on 2, $(Au_{20}(PET)_{15})_2$(dg). A sample (1.558 mg) was heated at a ramp of 10° C./min with $N_2$ flow rate of 55 mL/min. Mass loss percent corresponds closely to percent of organic matter in 2 (actual loss: 36.40%, expected loss: 35.0%), which is roughly equivalent to the percent of organic matter in 1.

This model reconciles the identical mass spectroscopy for 1 and 2, as the diglyme linkage does not survive MALDI ionizing conditions. It explains the size exclusion chromatography showing 2 as approximately double the size of 1. The smaller than expected size measured for 2 may arise from a non-spherical shape, as well as dissociation during the duration of the chromatography experiment. The model explains the presence of oxygen in this sample by X-ray photoelectron spectroscopy (XPS) (FIG. 9), the appearance of additional features in the IR spectrum of 2, and the additional feature in the DSC of 2. The assignment is also supported by thermogravimetric analysis (TGA) of 2 which confirms the expected amount of organic matter in the formula $(Au_{20}(PET)_{15})_2(dg)$ (FIG. 10: actual loss 36.4%, expected loss 35.0%).

Alternate explanations to account for the reversible conversion of 1 and 2 were considered. Isomerization is ruled out by size exclusion chromatography which indicates a higher molecular weight for 2 than can be consistent with isomerization. We also considered the possibility that 1 and 2 are redox pairs, but observed that the clusters exhibit irreversible electrochemical behavior as determined by differential pulse voltammogram analysis. The likelihood of the diglyme induced dimerizarion model was further investigated through density functional theory (DFT) modeling.

For DFT modeling we considered the previously published theoretical structure of $Au_{20}(SR)_{16}$ (Pei et al., *J. Am. Chem. Soc.* 2009, 131, 13619) and replaced a single —SR ligand with a diglyme and the rest of —SR by —SMe (Me=methyl). A relaxed structure of such $(Au_{20}(SMe)_{15})_2$-dg is shown as inset to FIG. 5 and further details are provided in Example 1 below. In the relaxed structure, the terminal methoxy groups of diglyme interact weakly via oxygen lone pair orbitals with gold atoms that are part of extended, protecting MeS—Au—Au—SMe units of each cluster. These two gold atoms in the units are proximal to the methoxy oxygen and have a typical metal-metal distance of 2.64 Å.

Figure 5:
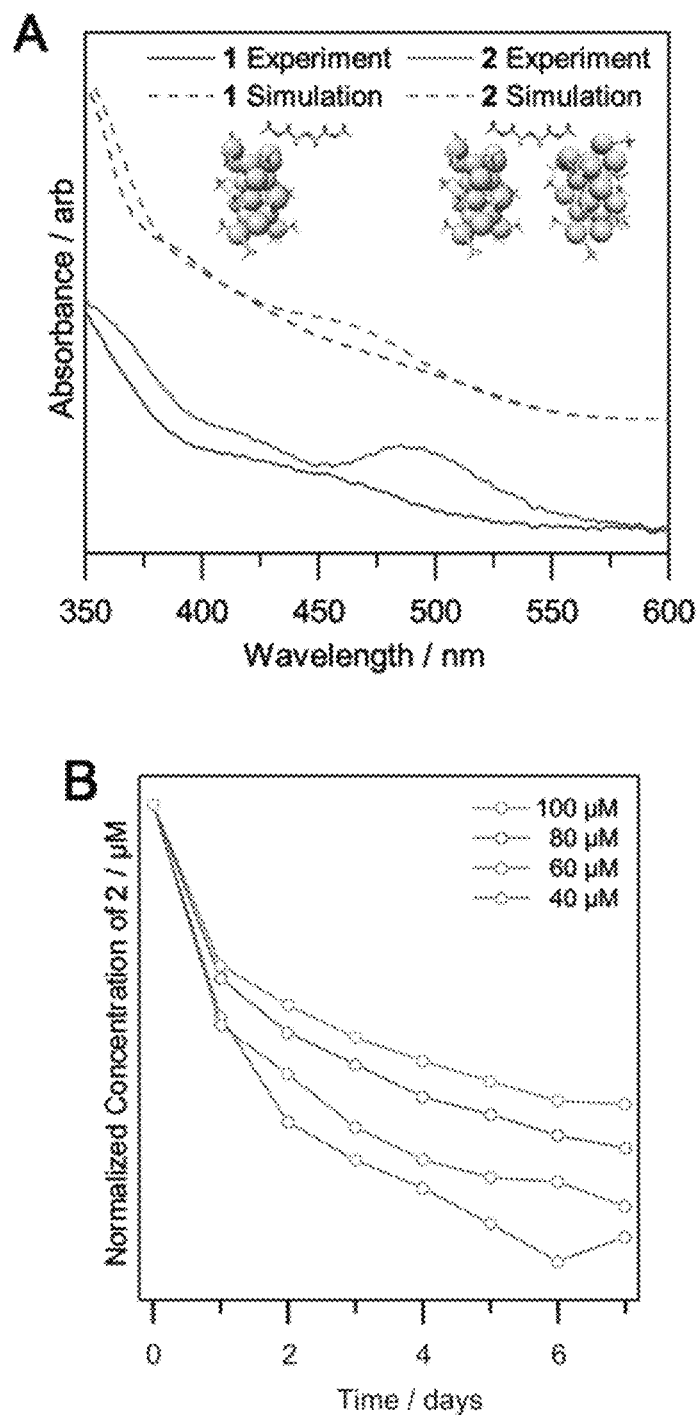
FIG. 5. The optical spectra of 1 and 2 allow monitoring of their interconversion.
Figure 11:
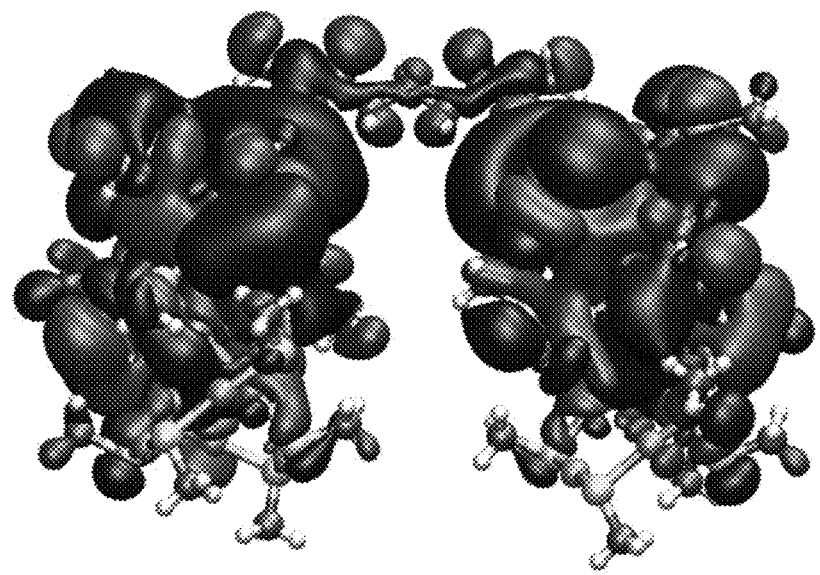
FIG. 11. Combined orbital contours of the twice-degenerate HOMO of the computed diglyme-linked $Au_{20}(SMe)_{15}$ dimer.

The diglyme-mediated binding of the clusters is close to thermoneutral but very slightly endothermic by 0.07 eV (6.8 kJ/mol). However, this estimate does not take into account the solvent effects. While the electronic structure of a single $Au_{20}(SMe)_{16}$ cluster shows a zero-spin ground state configuration stabilized by a large HOMO-LUMO gap, the calculations surprisingly predict a spin-triplet ground state for $(Au_{20}(SMe)_{15})_2dg$. The twice-degenerate HOMO orbital of the dimer is delocalized over the large part of the system including the carbon-oxygen backbone of the linker (FIG. 11). Computed optical spectra of $Au_{20}(SR)_{16}$ monomer and $(Au_{20}(SMe)_{15})_2dg$ dimer are rather similar except for a distinct broad peak for the dimer at around 470 nm, which compares rather well to the observed peak at 484 nm for 2 (FIG. 5).

Figure 12A:
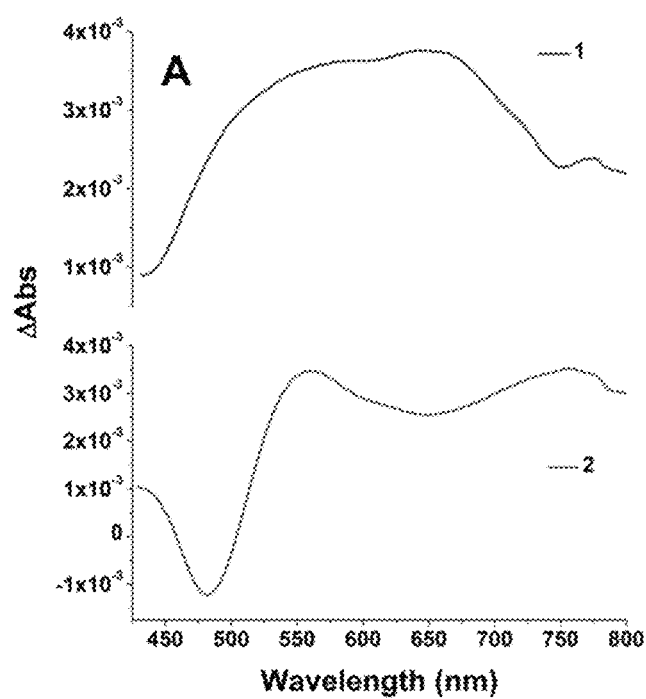
FIG. 12. Femtosecond transient absorption pump-probe results for 1 and 2 dispersed in tetrahydrofuran following 400-nm excitation (800 nJ/pulse). (A) Transient absorption spectra of 1 (upper graph) and 2 (lower graph) recorded at 1-ps pump-probe time delay. Species 2 exhibited a prominent transient bleach at 485 nm. (B) Comparison of time-dependent differential amplitude at 625-nm probe wavelength for 1 (open circles) and 2 (solid circles). Species 2 included an approximately 100 ps transient absorption growth not detected for species 1. (C) Summary of electronic relaxation time constants for species 1 plotted versus probe wavelength. (D) Bleach recovery kinetics monitored at 485 nm for species 2. (E) Normalized difference between co- and counter-circularly polarized transient absorption signal (black) monitored at 485 nm plotted versus pump-probe time delay along with the fit result for a first-order exponential decay. The fit yielded a 1.56±0.24 ps time constant, which was attributed to a spin-flip-relaxation process.
Figure 13:
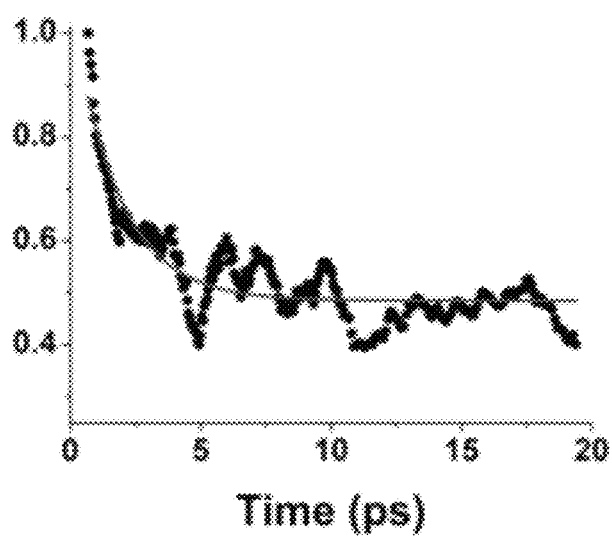
FIG. 13. Femtosecond transient absorption pump-probe results for 1 and 2 dispersed in tetrahydrofuran following 400-nm excitation (800 nJ/pulse). Normalized difference between co- and counter-circularly polarized transient absorption signal (black) monitored at 485 nm plotted versus pump-probe time delay. The fit yielded a 1.56±0.24 ps time constant, which was attributed to a spin-flip-relaxation process.

We validated the theoretical predictions of a zero-spin multiplicity for 1 and triplet-spin multiplicity for 2 through femtosecond time-resolved transient absorption pump-probe measurements to compare the electronic relaxation dynamics oil and 2. Electron relaxation dynamics were observed as dramatically different between 1 and 2 (FIG. 12). We studied both nanocluster species using co- and counter-circularly polarized pump and probe laser pulses, which is an established method for isolating spin-dependent dynamics (Baumberg et al., *Phys. Rev. Lett.* 1994, 72, 717). The difference between co- and counter-circularly-polarized transient absorption data monitored at 484 nm for 2 is shown in FIG. 13. These data revealed a spin-dependent relaxation process with a decay time constant of 1.56±0.24 ps, which was not detected for 1. This relaxation process, which was observable only by using appropriate laser pulse polarizations, is attributed to a spin-flip mechanism that is unique to the high-spin dimer species. Taken together, the distinguishable transient difference spectra, along with the electronic and spin-dependent relaxation dynamics of 2 confirm the experimental and theoretical aspects of the model.

Thus, the invention provides assemblies of weak-solvent mediated dynamic gold nanoparticles (AuNPs). The dynamic and environmentally responsive AuNPs can be used in various applications including catalysis, optics, fluorescent probes, theranostics, diagnostics, MRI/CT contrast agents, photothermolysis of cancer cells and tumors, optical bioimaging of cells and tissues, toxic molecule detection, and biolabeling, for example, to take advantage of properties that arise from spatial-close coupling of gold nanoclusters.

DEFINITIONS

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York. N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein, it is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution or in a reaction mixture.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

A "gold mine-cluster" refers to a gold nanoparticle that is composed of fewer than 100 gold atoms, where the nanoparticle has a diameter of less than about 3 nm. Because of their quantized electronic structure and geometrical structures, gold nanoclusters exhibit unique properties that are significantly different from their larger counterparts (see Tsukuda, *Bull. Chem. Soc. Jpn.*, 2012, 85, 151). Ligand passivated gold nanoclusters having ligands with hydrophilic moieties can be highly water-soluble. Ligand passivated organo-soluble gold nanoclusters can be soluble in organic solvents such as carbon tetrachloride, chloroform, methylene chloride, THF, toluene, and the like.

A "gold compound" refers to a molecule comprising gold atoms (e.g., an auric salt) that can be combined with an organic thiol followed by reduction in a weak ligand to provide a gold nanoparticle as described herein. Examples of suitable gold compounds include auric salts and auric oxides such as $HAuCl_4 \cdot xH_2O$ (where x is usually 3 but can vary), $KAuCl_4$, $AuCl_3$, $Au(OH)_3$, their related congeners such as $AuBr_3$, and other aurates known in the art.

As used herein, a "thiol" refers to an organic compound that includes at least one "—SH" group, which is typically a primary or secondary thiol group, and which can be used as a ligand for passivating the surface of a gold nanocluster, thereby forming thiolates on the nanocluster surface. The thiol can be a water-soluble thiol or organic-soluble thiol.

Examples of suitable water-soluble thiols include, but are not limited to, glutathione, cysteine, captopril, thiomalic acid, N-(2-mercaptopropionyl)glycine, p-mercaptobenzioc acid, m-mercaptobenzoic acid, furan-2-ylmethanethiol, penicillamine, $(C_2-C_7)$ mercaptoalkanoic acids such as 6-mercaptohexanoic acid, and the like.

Examples of suitable organo-soluble thiols include, but are not limited to, 2-phenylethanethiol (PET), 1-phenylethanethiol, benzyl mercaptan, thiophenol, $(C_1-C_{18})$alkylthiols such as methanethiol, isopropylthiol, t-butyl thiol, hexanethiol and dodecanethiol, $(C_8-C_{18})$mercaptoalkanoic acids such as 11-mercaptoundecanoic acid, $(C_3-C_8)$mercaptocycloalkanes such as cyclohexanethiol, dimercaptosuccinic acid, 2-mercaptoethanol, 3-mercaptopropanol, 3-mercaptopropane-1,2-diol (2,3-dihydroxypropylmercaptan; thioglycerol), 1-adamantanethiol, 1-naphthalenethiol, 2-naphthalenethiol, camphorthiol, and the like. Some organo-soluble thiols such as those having a carboxylic acid functionality may become water soluble at high pH.

Thiolates on the surface of gold nanoclusters typically comprise about 1-30 carbon atoms and may have a wide variety of functional groups such as oxo (e.g., carbonyl, aldehyde, or ketone) moieties, carboxylic acids, anhydride moieties, ester moieties, amide moieties, cyano, nitro, inorganic acid derivatives (e.g., phospho and boro acids and derivatives) and their sulfur and amino analogs, including I°, II°, III°, and IV° amines, zwitterionic moieties, and various substituents where the substituents may be hydrocarbon or substituted hydrocarbon, as well as carbocyclic and heterocyclic, with functional groups coming within the groups set forth above, as well as nitrogen derivatives, such as azo, azoxy, and diazo, organic and inorganic salts of the above ions, and the like. Complex thiolates may be used, both naturally occurring and synthetic, including oligomers, e.g., oligopeptides, of from about 2 to 30 units, thio analogs of purines, pyrimidines, nucleotides and nucleosides, aptamers, and amide linked nucleic acid analogs.

In some embodiments, the thiolates can be monomercapto thiolates including thiol substituted carboxylic acids, e.g., p-mercaptobenzoic acid, and other mercaptoaromatic carboxylic acids of from 5 to 20, usually 7 to 20, carbon atoms and from 0 to 4 heteroatoms, carbocyclic or heterocyclic, generally having from 5 to 6 annular members, as well as being optionally substituted by the above indicated groups, that may be present as annular atoms or as substituents, mercaptoalkanoic acids of from 3 to 20 carbon atoms, where the mercapto group is distant from the carboxy group, being separated by at least 2 carbon atoms, for a 1-carboxy compound, at least at the 3-carbon, amino acids, e.g., cysteine, mercaptobenzonitriles, tiopronin, glutathione, CoA, thiosugars, and the like. In some embodiments, one thiolate will be preferred to another and various stabilities may be obtained depending upon the particular thiolate used.

As used herein, "water-soluble" refers to a compound that is freely soluble in water or that is soluble in water in the presence of a base. As used herein, "organo-soluble" or "organic-soluble" refers to a compound that is soluble in organic solvents and is insoluble in water or only slightly water soluble. A compound that is only slightly water-soluble has a solubility of less than 0.1 mg/mL and preferably less than 0.05 mg/mL in water at 25° C. A compound that is water insoluble has a solubility of less than 0.01 mg/mL in water at 25° C. However, both water-soluble and organo-soluble compounds (and intermediary compounds) can all be used as compounds for the organic layer of a gold nanocluster as described herein.

A "weak ligand" or "weak gold nanoparticle ligand" refers to an organic molecules that contains weak gold-binding heteroatom moieties such as ethers, thiol ethers, amines and/or phosphines. Examples of weak ligands that can be used as the solvents in the gold nanocluster-forming reaction and therefore linking agents of the gold nanoclusters described herein include compounds of Formula I:

(I)

wherein

X is O, S, CH$_2$, NH, or PH;

R$^1$ and R$^2$ are each independently OH; (C$_1$-C$_8$)alkoxy such as OMe and OEt; SH; (C$_1$-C$_8$)alkylthio such as SMe and SEt; NR$^x_2$ where R$^x$ is H or (C$_1$-C$_8$)alkyl, such as NH$_2$, NHMe, NMe$_2$, NHEt, and NEt$_2$; PR$^x_2$ where R$^x$ is H or (C$_1$-C$_8$)alkyl such as PH$_2$, PHMe, PMe$_2$, PHEt, and PEt$_2$; and n is 1, 2, 3, 4, or about 5 to about 100 (e.g., about 10, about 20, about 30, about 40, or about 50). In certain specific embodiments, the compound of Formula I is diglyme, triglyme (triethylene glycol dimethyl ether), or tetraglyme (tetraethylene glycol dimethyl ether). In other embodiments, the compound of Formula I does not include a sulfur atom.

In one specific embodiment, X is O. In another specific embodiment, X is one of S, CH$_2$, NH, and PH. In another specific embodiment, R$^1$ is OMe. In another specific embodiment, R$^2$ is OMe, SH, or SMe. In various embodiments, n can be 1. In some embodiments, n can be 2, 3, or 4. In other embodiments, n can be 5 to about 50, and any increment of 5 from 5 to 40 to about any increment of 5 from 10 to 50 (e.g., 5-10, 5-15, 5-40, 5-50, 40-50, 45-50, or 20-40).

Au$_{20-28}$ Nanoclusters.

The invention described herein includes several types of novel gold nanoclusters and methods for their synthesis. As a class, the Au$_{20-28}$ gold nanoclusters exhibit excellent quantum yield of fluorescence and lifetime. The Au$_{20-28}$ gold nanoclusters can have a quantum yield (# of photons emitted/# photons absorbed) of about 2-4×10$^{-3}$ (e.g., about 0.2-0.4% of the photons are re-emitted). For example, the glutathione-protected gold nanoclusters described herein (e.g., Au$_{25}$(GS)$_{17}$(diglyme)) have a quantum yield of 3×10$^{-3}$ (0.3% of the photons are re-emitted), whereas the known Au$_{25}$(GS)$_{18}$ nanocluster has a quantum yield of only 1×10$^{-3}$ or 0.2% (re-emitted photons).

One aspect of the invention includes the use of a weak gold nanoparticle ligand such as diethylene glycol dimethyl ether ("diglyme") as a solvent, co-solvent, or in large excess for the synthesis reaction. A large excess of the weak ligand refers to at least about 50 equivalents of the weak ligand with respect to the equivalents of thiol compound used for the passivating layer of organic material. A typical excess can be at least about 100 equiv, at least about 150 equiv, at least about 200 equiv, up to several thousand equivalents, at which point the dilution may slow the reaction.

Another aspect of the invention includes novel compounds (e.g., gold nanoclusters) that are comprised of a unique combination of Au atoms, a finite number of thiol ligands, and a weak ligand ("WL") (e.g., Au$_{20}$L$_{15}$WL, Au$_{24}$L$_{17}$WL, Au$_{25}$L$_{17}$WL, or Au$_{28}$L$_{19}$WL). The compounds are stable and can have specific colors that are dependent upon a dynamic equilibrium between a monomeric nanocluster and a dimeric nanocluster (e.g., (Au$_{20}$L$_{15}$)$_2$WL, (Au$_{24}$L$_{17}$)$_2$WL, (Au$_{25}$L$_{17}$)$_2$WL, or (Au$_{28}$L$_{19}$)$_2$WL, where WL acts as a linking ligand between the two monomeric nanoclusters of the dimer).

Another aspect of the invention includes Au/ligand nanoclusters wherein one or more of the ligands is a weak gold nanoparticle ligand such as diglyme. The diglyme may chelate to the nanocluster via 1, 2, or 3 of its three oxygen atoms; other weak ligands may chelate to the nanocluster via 1, 2, 3 or more heteroatoms. The weak ligands may also chelate to more than one gold nanocluster, thereby forming a dimer.

In one embodiment, for the preparation of a water-soluble gold nanoparticle (a gold nanoclusters passivated with glutathione (SGH)), a general overall reaction equation can be represented by equation (1).

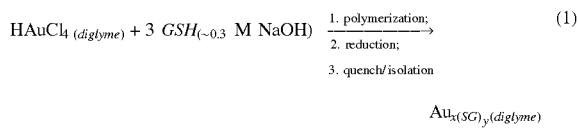

$$\text{HAuCl}_4 \text{ (diglyme)} + 3 \text{ GSH}_{(\sim 0.3 \text{ M NaOH})} \xrightarrow[\substack{\text{2. reduction;}\\\text{3. quench/isolation}}]{\text{1. polymerization;}} \text{Au}_{x}(SG)_{y}(\text{diglyme}) \quad (1)$$

where x=20-28 y=15-19 (typically x=25 y=17 for glutathione-protected nanoclusters). The glutathione can be exchanges for other water-soluble or organic-soluble thiols, and the diglyme can be exchanged for other weak gold nanocluster ligands. The polymerization is initiated by combining the gold compound and an excess of an organic thiol (e.g., about 3 equiv) in a large excess of a weak gold ligand such as diglyme (optionally in combination with an additional organic solvent such as THF). When a water-soluble organic thiol is used, a base such as an alkali metal or alkaline earth metal hydroxide can be used to facilitate dissolution. The polymerization can typically be carried out at room temperature (~23° C.), or at slightly elevated temperatures (e.g., 30-40° C.), for about 0.5 hours.

The polymerized material can then be reduced with an effective reducing agent, such as a hydride. The reductant is commonly a water-compatible metal hydride, such as the alkali metal Group III metal hydrides, such as sodium borohydride, lithium borohydride, lithium aluminium hydride, sodium cyanoborohydride, sodium trimethoxyborohydride, lithium trimethoxyborohydride, and the like, or other reducing compounds that are compatible with the reaction mixture and provide products that are compatible with isolating the AuNCs. Generally at least stoichiometric, usually excesses, of the hydride will be used, usually at least about 1.2-fold excess and not more than about 20-fold excess, usually not more than about 10-fold excess. For example, in some embodiments, the amount of sodium borohydride can be about 0.05 equiv (e.g., for preparation of water-soluble gold nanoclusters) to about 1 or 2 equiv (e.g., for preparation of organo-soluble gold nanoclusters) (equivalents based on amount of gold atoms). The hydride can be added neat (0% solvent) or dispersed in an aqueous solvent system (e.g., water optionally in combination with an organic solvent such as diglyme) at a convenient concentration and volume, usually not more than about 40%, often not more than about 25%, of the volume of the reaction medium, for the preparation of organo-soluble gold nanoclusters. For example, for the preparation of organo-soluble gold nanoclusters, the NaBH$_4$ in diglyme volume can be about 2-10%, or about 4-5% of the totally reaction volume. However, for the preparation of water-soluble gold nanoclusters, the NaBH$_4$ in diglyme volume can be higher, such as about 60-80% of the totally reaction volume. The reducing agent can be combined with the intermediate for about 1 hour at room temperature. A greater or lesser amount of time can be employed, and the temperature can be increased or decreased based on specific reagents and reaction parameters, as would be recognized by one of skill in the art.

Generally, the reaction medium will be diluted with an appropriate solvent (e.g., an alkanol such as methanol, ethanol, or isopropanol) to provide a precipitating medium. Because of the high solubility of some AuNCs in water, particularly basic water, the amount of the alkanol necessary for precipitation will vary with the hydroxide concentration and the choice of alkanol. Reduced temperatures below room temperature can be employed to facilitate precipitation and isolation.

Organo-soluble gold nanoparticles can be prepared simply by exchanging the water-soluble thiol (e.g., GSH) for an organo-soluble thiol such as PET. For organo-soluble thiols, the base can be omitted from the reaction described above. The product may then be isolated by filtration, centrifugation, and/or chromatography or other techniques available to those of skill in the art.

To obtain different passivating layers, the reaction may be run utilizing a variety of different thiol ligands. Other water-soluble ligands can utilize the same or similar synthesis as used for the Au/glutathione nanoclusters. Other organo-soluble ligands can utilize the same or similar procedure as described for the Au/phenylethanethiol nanoclusters. Slight modifications can be used to provide more atomically monodisperse products for each synthesis.

Purification of the resulting products from these reactions may be performed using a variety of techniques including polyacrylamide gel electrophoresis (PAGE). Once a product has been run on PAGE, the individual clusters can be separated. A cluster of interest may be cut out of the gel with a razor blade and extracted in water or suitable solvent in which the nanoclusters are soluble; drying yields a pure solid cluster.

Other embodiments of the invention include the synthesis of gold nanoclusters that may be accessed via ligand exchange reactions of different feed ratios or combinations of different thiol ligands. The surface properties of these clusters can be altered depending on the incoming ligand. Ligand exchange reaction may be run subsequent to the above described reactions. Thiol-for-thiol ligand exchange reactions are well known in the field and may be conducted via established protocols. For example, 18-mercapto-3,6,9,12-tetraoxaoctadecan-1-ol may be substituted for SG using an established ligand exchange procedure. Useful ligand exchange techniques and other useful gold nanocluster techniques are described by U.S. Pat. No. 8,304,257 (Ackerson et al.).

Additional aspects of the water-soluble ligand gold nanocluster syntheses include that preferably, the reaction is mixed by shaking rather than stirring. Preferably, the hydride reducing agent is added rapidly and all at once (e.g., poured and not dropwise). In various embodiments, the concentration of a borohydride reagent used can be about 0.2 mM to about 0.5 M, typically about 0.2 mM to about 0.5 mM. Anhydrous solvents should be used and stored over molecular sieves or otherwise kept anhydrous.

The descriptions above can be varied as would be readily recognized by one of skill in the art. Certain parameters may be varied and still remain within the scope of the current invention. These parameters include but are not limited to the following aspects. Reaction volume and weak ligand (e.g., 'glyme') concentration may be varied. The amount of organic solvent used to quench the reaction may be varied (50 mL is convenient for subsequent centrifugation, but more or slightly less is feasible). The centrifugation method described was limited by the performance of the available equipment; altering the speed, temperature and time will not affect the product formed but may change how long it takes to precipitate the product. Reduced pressure (e.g. vacuum) can be used to dry product instead of air drying. Voltage and time run for PAGE can be tuned for optimal separation of products; the cited conditions were merely optimized for the instruments used. Shaking vigor can be altered with no known effect on product formed.

The glyme solvent that is used may also be varied, as described above and herein below. A preferred glyme is diglyme (diethylene glycol dimethyl ether), but glymes of longer length may be used, including the glymes of Formula I, including triglyme (triethylene glycol dimethyl ether) and tetraglyme (tetraethylene glycol dimethyl ether). The length of the glyme (e.g., as defined for Formula I) may be used to control the size of the gold nanocluster formed.

The benefits of the compositions and techniques described herein include but are not limited to their reproducibility, the scalability for total reaction volumes of 1 µL to L-scale, very fast reaction rates (reactions take on average 2% of traditional AuNC syntheses times; 1 h vs. 48 h), the reactions do not require a "focusing period" (standard methods typically require multiple days), they can be performed at room temperature, they provide for new, kinetically-stable compounds not yet previously known, and they provide a high yield (relatively uncommon in this field). Unoptimized reaction conditions typically provide yields of about 10-50% of pure gold nanoclusters, based on gold atom content. However, optimized conditions can provide yields as high as about 90% conversion with respect to gold atom content.

General Synthesis of $Au_{20-28}$ Nanoclusters

A general method for the preparation of $Au_{20-28}$ gold nanoclusters is as follows. A solution of a gold salt such as $HAuCl_4.3H_2O$ in a suitable solvent and weak ligand such as diethylene glycol dimethyl ether is mixed with a solution of the thiol of interest. The resulting solution is stirred or agitated for a period of time, typically up to about 5 hours. The solution can optionally be heated, for example, to about 30° C. or to about 40° C. A suspension of a reducing agent, typically a hydride such as $NaBH_4$, in the solvent/weak ligand (e.g., diethylene glycol dimethyl ether) is added to the reaction mixture and allowed to react until the reaction changes color (typically turning to orange, often in less than 1 minute). The resulting reaction mixture can be either quenched by the addition of an organic solvent or allowed to stir at room temperature for an additional period of time, such as about 1 hour. The product can be isolated by filtration, centrifugation, chromatography, or other suitable isolation techniques known to those of skill in the art. Visualization can be carried out using techniques such as gel electrophoresis (for water-soluble clusters) or thin layer chromatography (for organo-soluble clusters).

Applications of $Au_{20-28}$ Nanoclusters.

The ligand passivated gold nanoclusters described herein can be used for a variety of applications that take advantage of their optical, electronic, and structural, properties. Applications of the nanoclusters include use in catalysis, optics, fluorescent probes, theranostics, diagnostics, and MRI/CT contrast agents. The nanoclusters also have utility within the fields of genomics and biosensories, immunoassays and clinical chemistry, photothermolysis of cancer cells and tumors, targeted delivery of drugs and antigens, optical bioimaging of cells and tissues, toxic molecule detection, and biolabeling, among others. The novel nanoparticle assemblies also possess interesting electron delocalization effects that can be utilized in light harvesting systems, for both fundamental research and material applications.

In one embodiment, the gold nanoclusters can be used for site-specific biomolecule labeling. Useful techniques for labeling are known in the art and are well-described by Ackerson et al. (*Methods in Enzymology*, 2010, 481, 195-230). The gold nanoclusters can also be used to study diagnostic imaging and therapy, including biological absorption, distribution, metabolism, excretion (ADME) and pharmacokinetics (PK); see Wong et al. (*Nanoscale*, 2013, 5, 10525-10533).

The following Examples are intended to illustrate the above invention and should not be construed to narrow its scope. One skilled in the art will readily recognize that the Examples suggest, many other ways in which the invention could be practiced. It should be understood that numerous variations and modifications may be made while remaining within the scope of the invention.

EXAMPLES

Example 1

Diglyme-Mediated Self-Assembly of Gold Nanoclusters

This example describes the assembly of gold nanoclusters into discrete and dynamic structures using the non-thiolate ligand diglyme as a weak ligand and crosslinker. The assembly and characterization of $Au_{20}(SC_2H_4Ph)_{15}$-diglyme and $Au_{20}(SC_2H_4Ph)_{15}$-diglyme-$Au_{20}(SC_2H_4Ph)_{15}$ is described in detail. The resulting assemblies possess useful optical, electronic, and structural properties.

Materials and Methods.

Chemicals.

Gold (III) chloride trihydrate ($HAuCl_4.3H_2O$, ACS reagent, ≥49.0% Au basis), sodium, borohydride ($NaBH_4$, powder, ≥98.0%) and 2-phenylethanethiol (PET, $PhCH_2CH_2SH$, ≥99%) were obtained from Sigma-Aldrich was used as received. Tetrahydrofuran (ACS reagent, ≥99.0%) and diethylene glycol dimethyl ether (dg, diglyme. anhydrous, 99.5%) were obtained from Sigma-Aldrich and stored over activated molecular sieves. Other solvents: methanol (ACS reagent, ≥99.8%), hexanes (anhydrous, 95%), dichloromethane (spectral grade, stabilized), chloroform (ACS reagent, stabilized). Silica gel used in chromatography: high-purity grade, pore size 60 Å, 2-25 µm particle size, without binder, pore volume 0.75 cm3/g, for thin layer chromatography (Sigma-Aldrich). Bio-Beads SX-1 (styrene divinylbenzene) beads were used for size exclusion chromatography: 1% crosslinkage, 40-80 µm bead size, 600-14,000 MW exclusion range. For electrochemistry, the supporting electrolyte used was tetrabutylammonium hexafluorophosphate ($TBAPF_6$, >98%) obtained from TCI Chemicals and recrystallized in methanol.

Instrumentation.

Absorbance in the ultraviolet-visible (UV-vis) range was measured using a NanoDrop 2000c Spectrophotometer and a Hewlett-Packard 8452A diode array spectrophotometer. Kinetics measurements were run on an Evolution 300 spectrophotometer from Thermo Electron with a custom sealed cuvette to prevent $CHCl_3$ from evaporating and preserving total solution concentration. The ratio of absorbance at 454 and 484 nm, local minimum and maximum for 2, was used to quantify the relative amount of 1 and 2 in mixtures as equilibrium was reached. In all measurements, the ratio of 1 and 2 (lowest and highest values, respectively) was found from pure material as soon as solutions were made. Ratio change over time was calculated under the assumption that the molecular weight of 1 and 2 were 5,997.7 and 11,995.4 Da, respectively. Together with the known extinction coefficients of 1 and 2 and 454 and 484 nm, this provided a quantifiable relative concentration of 1 and 2 in mixtures of the clusters.

Matrix-assisted laser desorption/ionization mass spectroscopy (MALDI-MS) spectra were obtained with a Bruker Ultraflex MALDI-TOF/TOF using the matrix trans-2-[3-(4-tert-butylphenyl)-2-methyl-2-propenylidene]malononitrile (DCTB). Solid sample was dissolved in a minimal amount of DCTB (10 mg/mL, $CHCl_3$). Typically, ~3 µL was sported on the place and allowed to air dry for 30 minutes. In order to guarantee reliable data, crystal-pure $Au_{25}(PET)_{18}$ was used to determine the optimal laser power, accelerating voltage, and detector gain to produce the most accurate spectrum. These identical parameters were then used to obtain spectra of 1 and 2. Spectra were collected in reflective positive mode for greatest resolution.

Infrared (IR) spectra of ~1 mg of solid samples were measured on a Thermo Nicolet 380 FT-IR (ATR on ZnSe).

A TA TGA 2950 Thermogravimetric analyzer was used for thermogravimetric analysis (TGA). Roughly 1.558 mg of sample was placed in a platinum pan. Temperature increased at 10° C./min to 400° C. and $N_2$ flow rate was kept at 55 mL/min.

A TA Modulated 2920 differential scanning calorimeter (DSC) was also used to measure thermal stability. For both 1 and 2, 1.5 mg of sample was used. Temperature increased at 10° C./min to 400° C. and $N_2$ flow rate was kept at 90 mL/min.

A PHI 5800 system was used to measure X-ray photoelectron spectra. Pure 2 was dissolved in $CHCl_3$ and spotted onto a polished stainless steel substrate. Charge was referenced to adventitious C1s at 284.4 eV.

Differential pulse voltammetry was performed in dichloromethane solutions containing 100 mmol $TBAPF_6$ using a CH Instruments CHI750D potentiostat.

The centrifuge used was an Eppendorf 5810R Centrifuge. The sonicator used to help $BH_4$ go into solution was a Digital Ultrasonic Cleaner UD50SH-2L.

Synthesis Au Nanoclusters 1 and 2.

A 250-mL Erlenmeyer flask was charged with 2-phenylethanethiol (48 mL, 100 mM, 4.8 mmol, 3 equiv.) in tetrahydrofuran and $HAuCl_4.3H_2O$ (16 mL, 100 mM, 1.6 mmol, 1 equiv.) in diethylene glycol dimethyl ether (diglyme) solution was added to the reaction flask. The reaction was stirred at rt (~22° C.) for 3 hours or until the cloudy yellow solution turned milky white. Five minutes prior to the end of the 3 hours, a suspension of $NaBH_4$ in diglyme (8 mL, 50 mM, 0.8 mmol, 0.5 equiv.) was sonicated at rt for 5 minutes. 120 mL of diglyme was added to the reaction vessel, followed by dropwise-addition of 8 mL of the $NaBH_4$ suspension over the course of 1 minute, which turned the reaction yellow/orange, indicating the formation of both $Au_{20}(PET)_{15}dg$ (1) and the dimer (2).

The reaction was allowed to stir at rt for an additional hour for a brief aging process. Precipitated by-products were filtered out using a Buchner funnel with medium frit, and the remaining orange solution was transferred to a 1-L bleaker. The reaction was quenched via the addition of methanol to 1 L, and the quenched solution was split into 20 50-mL polypropylene centrifugation conicals. The content of the conicals was then centrifuged in a swinging bucket rotor at 4,000 rpm and 4° C. for 10 minutes. The clear and colorless supernatant was then decanted and the orange precipitate was air-dried. Thin layer chromatography was run using 9:11 hexanes:chloroform to characterize the product. The orange and yellow nanocluster bands were visible by eye, thus no staining steps were performed for visualization.

Purification of Au Clusters.

Normal phase silica gel flash column chromatography was used to separate out the crude clusters with no prior purification necessary. A solution of 9:11 hexanes:chloroform was used as the mobile phase. Fractions were collected directly into methanol-filled and $LN_2$-chilled glass centrifugation tubes. This causes the clusters to precipitate out of solution immediately once eluted form the column in order to prevent interconversion. Spinning the tubes containing product at 3000 rpm (maximum for our glass tubes) for 5 minutes at 4° C. sediments the clusters to the bottom and the clear supernatant is discarded. Products are then air dried in the centrifugation tubes. This results in very pure $Au_{20}(PET)_{15}(dg)$, 1, and $(Au_{20}(PET)_{15})_2(dg)$, 2, as yellow and orange powders, respectively. If the products are not immediately analyzed, they are stored under argon and kept in the dark to prolong cluster integrity.

For size exclusion chromatography, beads were allowed to swell in THF overnight. A 60-cm long (2.5 cm diameter) column was filled to roughly 40 cm with the swollen beads. Roughly 500 mL of THF was used to flush out any residual material before each separation took place. Pure samples were loaded onto the column and absorbance was measured on fractions collected in 15 second intervals (total volume of fractions was dependent on flowrate, which was empirically determined for each run, and was usually between 0.25 and 0.50 mL). Standards used for calibration were crystal-pure $Au_{25}(PET)_{18}$ and $Au_{144}(PET)_{60}$. It is important to note that this method is not suitable for isolation of pure compounds "as-is". Note that a much longer column would be necessary to fully separate 1 and 2 (since multiple runs are impossible to perform due to the relative concentration of 1 and 2 changing as sample is concentrated), and 1 was found to convert to 2 during the duration of the run.

Density Functional Theory.

Computations for the model structures were performed with density functional theory code GPAW (Enkovaara et al., *J. Phys. Condens. Matter* 22, 253202 (2010)), which implements projector-augmented wave method in a real-space grid. The real space had a grid spacing 0.2 Å. $Au(5d^{10}6s^1)$, $S(3s^23p^4)$, $C(2s^22p^2)$, $O(2s^22p^4)$ and $H(1s^1)$ electrons were regarded as the valence, and the PAW setups for Au included scalar-relativistic corrections. Total energies were evaluated at the GGA-PBE level (gradient-corrected functional of Perdew, Burke and Ernzerhof) (*Phys. Rev. Lett.* 77, 3865-3868 (1996)). All calculations were spin-polarized. All the atoms were relaxed during the geometry optimization until the maximum force acting on atoms below 0.05 eV/Å. Optical absorption spectra were calculated with the PBE level using spin-polarized linear-response (LR) time-dependent DFT (LR-TDDFT) formalism in GPAW (Walter et al., *J. Chem. Phys.* 128, 244101 (2008)).

Spectroscopy.

The femtosecond pump-probe laser system has been described previously (Dowgiallo et al., *Nano Lett* 11, 3258-3262 (2011)), and the following details are provided as supporting information. Both species 1 and 2 were excited using the 400-nm second harmonic of an amplified Ti:sapphire laser, and transient spectra and dynamics were recorded using temporally delayed continuum laser pulses. The polarization state of the pump and probe laser pulses was set using a combination of linear polarizers and wave plates. Transient dynamics were analyzed using software program written in house. The data acquisition time for each pump-probe measurement was less than one hour. A fresh sample was used in a flow cell for each scan to avoid decomposition.

We validated the theoretical predictions of a zero-spin multiplicity for 1 and triplet-spin multiplicity for 2 through femtosecond time-resolved transient absorption pump-probe measurements to compare the electronic relaxation dynamics of 1 and 2. Consistent with both linear absorption and theoretical calculations (FIG. 5), the differential absorption spectrum of 2, resulting from 400-nm excitation, showed a prominent transient bleach centered at 484 nm and broad excited-state absorption (ESA) at longer wavelengths (FIG.

12A). In contrast, the transient difference spectrum of 1 consisted only of broad ESA; the transient bleach at 484 nm was specific to 2.

The electronic relaxation dynamics (FIG. 12B) of 1 were fit using two components: i) a first-order picosecond ESA growth, and ii) a non-decaying plateau that persisted for the three nanosecond dynamic range of the transient absorption measurement. The ESA growth component exhibited a probe wavelength dependence that was consistent with internal electron thermalization processes (FIG. 12C). In contrast to 1, species 2 exhibited multiple relaxation components. FIG. 12D portrays the relaxation dynamics obtained by monitoring the amplitude of the differential response at 484 nm for 2 following excitation by linearly polarized 400-nm light. The transient bleach was fit to a recovery time constant of 260±50 ps; a non-decaying plateau function was also included to accurately fit the data. Monitoring the electronic relaxation dynamics of 2 at 625-nm probe wavelength (FIG. 12B, solid circle trace) revealed an approximately 100 picosecond ESA growth; these time domain data were clearly different from those obtained from 1 at the same probe wavelength (FIG. 12B, open circle trace).

In order to examine whether the dramatic differences in electronic energy relaxation of 1 and 2 originated from the theoretically predicted high-spin configuration of 2, we studied both nanocluster species using co- and counter-circularly polarized pump and probe laser pulses, which is an established method for isolating spin-dependent dynamics (Baumberg et al., *Phys. Rev. Lett.* 12, 717-720 (1994)). The difference between co- and counter-circularly-polarized transient absorption data monitored at 484 nm for 2 is shown in FIG. 12Es. These data revealed a spin-dependent relaxation process with a decay time constant of 1.56±0.24 ps, which was not detected for 2. This relaxation process, which was observable only by using appropriate laser pulse polarizations, is attributed to a spin-flip mechanism that is unique to the high-spin dimer species. Taken together, the distinguishable transient difference spectra, along with the electronic and spin-dependent relaxation dynamics of 2 confirm the experimental and theoretical, aspects of the model.

Example 2

Preparation of Organs-Soluble $Au_{20}SR_{15}$(Weak Ligand) Nanoclusters

Organo-soluble $Au_{20}SR_{15}$(weak ligand) nanoclusters can be prepared as follows.

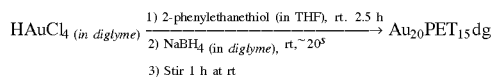

A glass flask is charged with 3 equivalents of phenylethanethiol (PET) (e.g., 4.8 mmol, 48 mL of 100 mM solution) in tetrahydrofuran. One equivalent of $HAuCl_4 \cdot 3H_2O$ (e.g., 1.6 mmol, 16 mL) in diethylene glycol dimethyl ether solution is also added to the reaction flask. The reaction is stirred at about 0-30° C. (typically about room temperature) for roughly 2.5 hours or until the cloudy yellow solution turns a milky white. Prior to the end of the 2.5 hours (e.g., about 5 minutes prior), a suspension of 200 mM $NaBH_4$ in diethylene glycol dimethyl ether (about 10 mL) is sonicated, optionally at room temperature, for about 5 minutes. Diethylene glycol dimethyl ether (120 mL) is added to the reaction vessel, followed by 8 mL of the $NaBH_4$ (1.6 mmol, 1 equiv) suspension. A color change is typically observed (orange, when preferable conditions and the reagents above are used, which indicates the formation of $Au_{20}(PET)_{15}$ nanoclusters). The reaction is allowed, to stir for a brief aging process (typically at room temperature for about 1 hour). Precipitates (by-products) are filtered out using a Büchner funnel, and the remaining orange solution is transferred to a 1-L reaction vessel.

The reaction is quenched via the addition of an organic solvent (such as isopropanol, ethanol, or acetonitrile, but preferably methanol) to 1 L total volume and the quenched solution is split into 20 50-mL polypropylene centrifugation conicals. The content of the conicals is then mixed and centrifuged in a swinging bucket rotor at about 4,000 rpm and 4° C. for about 30 minutes. The clear and colorless supernatant is then decanted and the orange precipitate is dried under vacuum or in open atmosphere.

Thin layer chromatography may be run using chloroform: hexanes mixtures as mobile phase to characterize the product. The nanocluster bands are visible by ocular inspection and with a UV transilluminator, thus no staining steps are required for visualization. The visible products can be yellow, orange, pale blue, purple, brown, and black. Typical yields of $Au_{20}(PET)_{15}$(dg) are about 20-25%. Rf (9:11 hexanes:chloroform)=0.46 (dimer; orange), 0.52 (monomer; yellow) (weak ligand=diglyme); 0.61 (dimer; orange), 0.64 (monomer; yellow) (weak ligand=triglyene). Rf values were achieved after three consecutive TLC development runs. Gold nanocluster size can range from about 0.5 nm to about 2 nm. In some embodiments, the monomer nanocluster diameter is approximately 0.7-1 nm (by size exclusion chromatography; roughly spherical shape), and the nanocluster dimer diameter is approximately 0.9-1.5 nm (more prolate shape than the monomer).

Additional organo-soluble gold nanoclusters can be prepared by exchanging the PET for alternate organo-soluble thiols, such as those described above, to provide various $Au_{20}SR_{15}$(dg) nanoclusters where SR is the alternate organo-soluble thiol. Also, further gold nanoclusters can be prepared by exchanging diethylene glycol dimethyl ether (dg) for an alternate weak ligand (e.g., a compound of Formula I) to provide various $Au_{20}SR_{15}$(wk lig) nanoclusters where "wk lig" (weak ligand) is the alternate weak ligand. These gold nanoclusters can provide nanoparticles with intense fluorescent properties and increased intensity of paramagnetic behavior compared to other similarly sized gold clusters such as $Au_{25}(GS)_{18}$. The products are typically readily soluble in various organic solvents, which makes them valuable candidates for catalysis and as microscopy contrast reagents.

Example 3

Preparation of Water-Soluble $Au_{20}SR_{15}$(Weak Ligand) Nanoclusters

Water-soluble $Au_{20}SR_{15}$(weak ligand) nanoclusters can be prepared as follows.

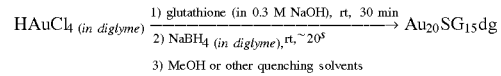

A non-glass vessel (typically a 50 mL polypropylene conical) is charged with three equivalents of glutathione (e.g., 6 mL 100 mM glutathione, 0.6 mmol) in a NaOH solution, preferably about 0.1-0.5 M, or about 0.3 M. One equivalent of HAuCl$_4$.3H$_2$O in diethylene glycol dimethyl ether solution (e.g., 0.2 mmol, 2 ml) is also added to the reaction vessel. The reaction is agitated at about 0-30° C. for about 5-300 minutes; shaking at room temperature for 30 minutes is preferable. Prior to the end of the agitations period (for example, about 5 minutes prior to the end of the 30 minute period), a suspension of about 0.5-100 (preferably about 0.5) mM NaBH$_4$ in dry diethylene glycol dimethyl ether (about 19 mL) is sonicated at room temperature for 5 minutes; longer sonication times and temperatures of up to about 40° C. are also suitable. A partial equivalent (about 0.043 equivalents) of the NaBH$_4$ suspension (preferably about 0.0085 mmol, 17 mL) is added to the reaction vessel. A color change will be observed, typically after approximately 5-60 seconds (orange will result when preferred conditions are used with the reagents above).

The reaction is then quenched by the addition of an organic solvent (such as isopropanol, ethanol, or acetonitrile, but preferably methanol) to a final volume of about 50 mL. The content of the reaction vessel is then mixed and then centrifuged in a swinging bucket rotor at about 4,000 rpm (at about 4° C.) for about 10 minutes. The typically clear and colorless supernatant can then be decanted and the orange precipitate can be dried under high vacuum or in open atmosphere. Gel electrophoresis visualization may be ran on a 30% polyacrylamide gel (19:1, acrylamide:bisacrylamide) at 175 V for 3 hours. The nanoparticle bands are visible by ocular inspection and with a UV transilluminator, thus no staining steps are needed for visualization. The visible products can be yellow, orange, green, pale blue, and brown. Typical yields of Au$_{25}$(GS)$_{17}$(dg) are about 20-25%. Gold nanocluster size can range from about 0.5 nm to about 2 nm.

Additional water-soluble gold nanoclusters can be prepared by exchanging the glutathione for alternate water-soluble thiols, such, as those described above, to provide various Au$_{25}$(GS)$_{17}$(dg) nanoclusters where SR is the alternate water-soluble thiol. Also, further gold nanoclusters can be prepared by exchanging diethylene glycol dimethyl ether (dg) for an alternate weak ligand (e.g., a compound of Formula I) to provide various Au$_{25}$SR$_{17}$(wk lig) nanoclusters where "wk lig" (weak ligand) is the alternate weak ligand. These gold nanoclusters can provide nanoparticles with intense fluorescent properties and increased intensity of paramagnetic behavior compared to other similarly sized gold clusters such as Au$_{25}$(GS)$_{18}$. The products are typically readily soluble in water, which makes them valuable candidates for biological studies.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A gold nanocluster of the formula Au$_x$(SR)$_y$(weak ligand), wherein x is 20-28, y is 15, 17, or 19, each R is independently an organic group comprising 1-30 carbon atoms covalently bound to the sulfur atom, and the weak ligand is a weakly associating gold ligand of Formula I:

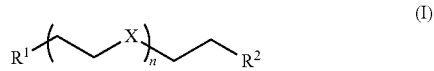

wherein
X is O, S, CH$_2$, NH, or PH;
R$^1$ and R$^2$ are each independently OH, OMe, OEt, SH, SMe, SEt, NH$_2$, NHMe, NMe$_2$, NHEt, NEt$_2$, PH$_2$, PHMe, PMe$_2$, PHEt, or PEt$_2$; and
n is 1, 2, 3, 4, or about 5 to about 50; and
wherein the nanocluster has an approximate molecular weight of 6 kDa and is yellow in color upon isolation.

2. The gold nanocluster of claim 1 further comprising a second gold nanocluster, thereby forming a discrete gold nanocluster of the formula (Au$_{20-28}$(SR)$_{15-19}$)$_2$(weak ligand), wherein the nanocluster has an approximate molecular weight of 10 kDa and is orange in color upon isolation.

3. The gold nanocluster of claim 2 wherein the diameter of the nanocluster is about 0.9 nm to about 2.5 nm.

4. The gold nanocluster of claim 1 wherein the nanocluster is water-soluble.

5. The gold nanocluster of claim 1 wherein the nanocluster is organo-soluble.

6. The gold nanocluster of claim 1 wherein x is 20, 24, 25, or 28.

7. The gold nanocluster of claim 1 wherein each R$^1$ and R$^2$ is OMe.

8. The gold nanocluster of claim 1 wherein n is 1, 2, or 3.

9. The gold nanocluster of claim 1 wherein the weak ligand of Formula I is diethylene glycol dimethyl ether, triethylene glycol dimethyl ether, or tetraethylene glycol dimethyl ether.

10. The gold nanocluster of claim 1 wherein —SR is the thiolate of glutathione, cysteine, captopril, thiomalic acid, N-(2-mercaptopropionyl)glycine, p-mercaptobenzioc acid, m-mercaptobenzoic acid, furan-2-ylmethanethiol, penicillamine, a (C$_2$-C$_7$)mercaptoalkanoic acid, 2-phenylethanethiol (PET), 1-phenylethanethiol, benzyl mercaptan, thiophenol, a (C$_1$-C$_{18}$)alkylthiol, a (C$_3$-C$_8$)mercaptocycloalkane, a (C$_8$-C$_{18}$)mercaptoalkanoic acid, dimercaptosuccinic acid, 2-mercaptoethanol, 3-mercaptopropanol, 3-mercaptopropane-1,2-diol, 1-adamantanethiol, 1-naphthalenethiol, 2-naphthalenethiol, or camphorthiol.

11. The gold nanocluster of claim 1 wherein —SR is the thiolate of glutathione or phenylethanethiol (PET).

12. The gold nanocluster of claim 1 wherein the quantum yield of a plurality of nanoclusters is at least about 2.5×10$^{-3}$.

13. The gold nanocluster of claim 1 wherein the diameter of the nanocluster is about 0.5 nm to about 1.5 nm.

14. A method of preparing the gold nanocluster of claim 1 comprising combining a gold compound, a thiol, and a weak ligand to form a first mixture, and contacting the first mixture with a reducing reagent to thereby form the gold nanocluster.

15. The method of claim 14 further comprising isolating the gold nanoclusters to provide a solid composition of the gold nanoclusters.

16. A gold nanocluster of the formula Au$_{20}$(SC$_2$H$_4$Ph)$_{15}$ (diethylene glycol dimethyl ether), wherein the nanocluster has an approximate molecular weight of 6 kDa and is yellow in color upon isolation.

17. The gold nanocluster of claim 16 further comprising a second gold nanocluster, thereby forming a discrete gold nanocluster of the formula $(Au_{20}(SC_2H_4Ph)_{15})_2$(diethylene glycol dimethyl ether), wherein the nanocluster has an approximate molecular weight of 10 kDa and is orange in color upon isolation.

18. A gold nanocluster of the formula $Au_{25}(SG)_{17}$(diethylene glycol dimethyl ether), wherein SG is the thiolate of glutathione, and the nanocluster has an approximate molecular weight of 6 kDa and is yellow in color upon isolation.

19. The gold nanocluster of claim 18 further comprising a second gold nanocluster, thereby forming a discrete gold nanocluster of the formula $(Au_{25}(SG)_{17})_2$(diethylene glycol dimethyl ether), wherein the nanocluster has an approximate molecular weight of 10 kDa and is orange in color upon isolation.

20. A gold nanocluster of the formula $Au_x(SR)_y$(weak ligand), wherein x is 20, 24, 25, or 28, y is 15, 17, or 19, each R is independently an organic group comprising 1-30 carbon atoms covalently bound to the sulfur atom, and the weak ligand is a weakly associating gold ligand of Formula I:

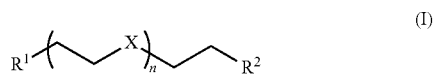

wherein

X is O, S, $CH_2$, NH, or PH;

$R^1$ and $R^2$ are each independently OH, OMe, OEt, SH, SMe, SEt, $NH_2$, NHMe, $NMe_2$, NHEt, $NEt_2$, $PH_2$, PHMe, $PMe_2$, PHEt, or $PEt_2$; and n is 1, 2, 3, 4, or about 5 to about 50; and wherein the nanocluster has an approximate molecular weight of 6 kDa and is yellow in color upon isolation.

21. The gold nanocluster of claim 20 wherein the weak ligand links to a second gold nanocluster of the same formula $Au_x(SR)_y$ as the first gold nanocluster.

* * * * *